United States Patent
Solis et al.

(10) Patent No.: US 12,254,586 B2
(45) Date of Patent: Mar. 18, 2025

(54) AUTO-FOCUS TOOL FOR MULTIMODALITY IMAGE REVIEW

(71) Applicant: Hologic, Inc., Marlborough, MA (US)

(72) Inventors: Herschel A. Solis, Santa Clara, CA (US); Calvin J. Wong, Fremont, CA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 17/939,015

(22) Filed: Sep. 7, 2022

(65) Prior Publication Data

US 2023/0125385 A1  Apr. 27, 2023

Related U.S. Application Data

(60) Provisional application No. 63/271,339, filed on Oct. 25, 2021.

(51) Int. Cl.
*G06T 3/40* (2024.01)
*A61B 5/00* (2006.01)
(Continued)

(52) U.S. Cl.
CPC .............. *G06T 3/40* (2013.01); *A61B 5/7425* (2013.01); *G06T 3/20* (2013.01); *G06T 7/11* (2017.01);
(Continued)

(58) Field of Classification Search
None
See application file for complete search history.

(56) References Cited

U.S. PATENT DOCUMENTS

| | | | |
|---|---|---|---|
| 3,502,878 | A | 3/1970 | Stewart |
| 3,863,073 | A | 1/1975 | Wagner |

(Continued)

FOREIGN PATENT DOCUMENTS

| | | |
|---|---|---|
| AU | 2014339982 | 4/2015 |
| CN | 1802121 A | 7/2006 |

(Continued)

OTHER PUBLICATIONS

European Extended Search Report in European Application 22203472.0, mailed Mar. 23, 2023, 8 pages.
(Continued)

*Primary Examiner* — Sultana M Zalalee
(74) *Attorney, Agent, or Firm* — Merchant & Gould P.C.

(57) ABSTRACT

Examples of the present disclosure describe systems and methods for an auto-focus tool for multimodality image review. In aspects, an image review system may provide for the display of a set of medical images representing one or more imaging modalities. The system may also provide an auto-focus tool that may be used during the review of the set of medical images. After receiving an instruction to activate the auto-focus tool, the system may receive a selection of an ROI in at least one of the images in the set of medical images. The auto-focus tool may identify the location of the ROI within the image and use the identified ROI location to identify a corresponding area or ROI in the remaining set of medical images. The auto-focus tool may orient and display the remaining set of medical images such that the identified area or ROI is prominently displayed.

19 Claims, 6 Drawing Sheets

(51) Int. Cl.
*G06T 3/20* (2006.01)
*G06T 7/11* (2017.01)
*G06V 10/25* (2022.01)

(52) U.S. Cl.
CPC .......... *G06V 10/25* (2022.01); *G06T 2200/24* (2013.01); *G06T 2207/10088* (2013.01); *G06T 2207/10132* (2013.01); *G06T 2207/20104* (2013.01); *G06T 2207/30068* (2013.01)

(56) References Cited

U.S. PATENT DOCUMENTS

| | | |
|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,557 A | 12/1985 | Keyes |
| 4,559,641 A | 12/1985 | Caugant et al. |
| 4,706,269 A | 11/1987 | Reina et al. |
| 4,727,565 A | 2/1988 | Ericson |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 6/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,099,846 A | 3/1992 | Hardy |
| 5,129,911 A | 7/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,219,351 A | 6/1993 | Teubner |
| 5,240,011 A | 8/1993 | Assa |
| 5,279,309 A | 1/1994 | Taylor et al. |
| 5,280,427 A | 1/1994 | Magnusson |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,386,447 A | 1/1995 | Siczek |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,499,097 A | 3/1996 | Ortyn et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino et al. |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,642,433 A | 6/1997 | Lee et al. |
| 5,642,441 A | 6/1997 | Riley et al. |
| 5,647,025 A | 7/1997 | Frost et al. |
| 5,657,362 A | 8/1997 | Giger et al. |
| 5,660,185 A | 8/1997 | Shmulewitz et al. |
| 5,668,889 A | 9/1997 | Hara |
| 5,671,288 A | 9/1997 | Wilhelm et al. |
| 5,709,206 A | 1/1998 | Teboul |
| 5,712,890 A | 1/1998 | Spivey |
| 5,719,952 A | 2/1998 | Rooks |
| 5,735,264 A | 4/1998 | Siczek et al. |
| 5,757,880 A | 5/1998 | Colomb |
| 5,763,871 A | 6/1998 | Ortyn et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz |
| 5,835,079 A | 11/1998 | Shieh |
| 5,841,124 A | 11/1998 | Ortyn et al. |
| 5,872,828 A | 2/1999 | Niklason et al. |
| 5,875,258 A | 2/1999 | Ortyn et al. |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,954,650 A | 9/1999 | Saito |
| 5,986,662 A | 11/1999 | Argiro |
| 6,005,907 A | 12/1999 | Ploetz |
| 6,022,325 A | 2/2000 | Siczek et al. |
| 6,067,079 A | 5/2000 | Shieh |
| 6,075,879 A | 6/2000 | Roehrig et al. |
| 6,091,841 A | 7/2000 | Rogers |
| 6,091,981 A | 7/2000 | Cundari et al. |
| 6,101,236 A | 8/2000 | Wang et al. |
| 6,102,866 A | 8/2000 | Nields et al. |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,215,892 B1 | 4/2001 | Douglass et al. |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,245,028 B1 | 6/2001 | Furst et al. |
| 6,272,207 B1 | 8/2001 | Tang |
| 6,289,235 B1 | 9/2001 | Webber et al. |
| 6,292,530 B1 | 9/2001 | Yavus |
| 6,293,282 B1 | 9/2001 | Lemelson |
| 6,327,336 B1 | 12/2001 | Gingold et al. |
| 6,327,377 B1 | 12/2001 | Rutenberg et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,424,332 B1 | 7/2002 | Powell |
| 6,442,288 B1 | 8/2002 | Haerer |
| 6,459,925 B1 | 10/2002 | Nields et al. |
| 6,463,181 B2 | 10/2002 | Duarte |
| 6,468,226 B1 | 10/2002 | McIntyre, IV |
| 6,480,565 B1 | 11/2002 | Ning |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |
| 6,638,235 B2 | 10/2003 | Miller et al. |
| 6,647,092 B2 | 11/2003 | Eberhard |
| 6,650,928 B1 | 11/2003 | Gailly |
| 6,683,934 B1 | 1/2004 | Zhao |
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,901,156 B2 | 5/2005 | Giger et al. |
| 6,912,319 B1 | 5/2005 | Barnes |
| 6,940,943 B2 | 9/2005 | Claus |
| 6,978,040 B2 | 12/2005 | Berestov |
| 6,987,331 B2 | 1/2006 | Koeppe |
| 6,999,553 B2 | 2/2006 | Livingston |
| 6,999,554 B2 | 2/2006 | Mertelmeier |

(56) References Cited

U.S. PATENT DOCUMENTS

| | | |
|---|---|---|
| 7,022,075 B2 | 4/2006 | Grunwald et al. |
| 7,025,725 B2 | 4/2006 | Dione et al. |
| 7,030,861 B1 | 4/2006 | Westerman |
| 7,110,490 B2 | 9/2006 | Eberhard |
| 7,110,502 B2 | 9/2006 | Tsuji |
| 7,117,098 B1 | 10/2006 | Dunlay et al. |
| 7,123,684 B2 | 10/2006 | Jing et al. |
| 7,127,091 B2 | 10/2006 | OpDeBeek |
| 7,142,633 B2 | 11/2006 | Eberhard |
| 7,218,766 B2 | 5/2007 | Eberhard |
| 7,245,694 B2 | 7/2007 | Jing et al. |
| 7,286,634 B2 | 10/2007 | Sommer, Jr. et al. |
| 7,289,825 B2 | 10/2007 | Fors et al. |
| 7,298,881 B2 | 11/2007 | Giger et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,406,150 B2 | 7/2008 | Minyard et al. |
| 7,430,272 B2 | 9/2008 | Jing et al. |
| 7,443,949 B2 | 10/2008 | Defreitas et al. |
| 7,466,795 B2 | 12/2008 | Eberhard et al. |
| 7,556,602 B2 | 7/2009 | Wang et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,630,533 B2 | 12/2009 | Ruth et al. |
| 7,634,050 B2 | 12/2009 | Muller et al. |
| 7,640,051 B2 | 12/2009 | Krishnan |
| 7,697,660 B2 | 4/2010 | Ning |
| 7,702,142 B2 | 4/2010 | Ren et al. |
| 7,705,830 B2 | 4/2010 | Westerman et al. |
| 7,760,924 B2 | 7/2010 | Ruth et al. |
| 7,769,219 B2 | 8/2010 | Zahniser |
| 7,787,936 B2 | 8/2010 | Kressy |
| 7,809,175 B2 | 10/2010 | Roehrig et al. |
| 7,828,733 B2 | 11/2010 | Zhang et al. |
| 7,831,296 B2 | 11/2010 | DeFreitas et al. |
| 7,869,563 B2 | 1/2011 | DeFreitas |
| 7,974,924 B2 | 7/2011 | Holla et al. |
| 7,991,106 B2 | 8/2011 | Ren et al. |
| 8,044,972 B2 | 10/2011 | Hall et al. |
| 8,051,386 B2 | 11/2011 | Rosander et al. |
| 8,126,226 B2 | 2/2012 | Bernard et al. |
| 8,155,421 B2 | 4/2012 | Ren et al. |
| 8,165,365 B2 | 4/2012 | Bernard et al. |
| 8,532,745 B2 | 9/2013 | DeFreitas et al. |
| 8,571,289 B2 | 10/2013 | Ruth |
| 8,594,274 B2 | 11/2013 | Hoernig et al. |
| 8,677,282 B2 | 3/2014 | Cragun et al. |
| 8,712,127 B2 | 4/2014 | Ren et al. |
| 8,787,522 B2 | 7/2014 | Smith et al. |
| 8,897,535 B2 | 11/2014 | Ruth et al. |
| 8,983,156 B2 | 3/2015 | Periaswamy et al. |
| 9,020,579 B2 | 4/2015 | Smith |
| 9,075,903 B2 | 7/2015 | Marshall |
| 9,084,579 B2 | 7/2015 | Ren et al. |
| 9,119,599 B2 | 9/2015 | Itai |
| 9,129,362 B2 | 9/2015 | Jerebko |
| 9,289,183 B2 | 3/2016 | Karssemeijer |
| 9,451,924 B2 | 9/2016 | Bernard |
| 9,456,797 B2 | 10/2016 | Ruth et al. |
| 9,478,028 B2 | 10/2016 | Parthasarathy |
| 9,589,374 B1 | 3/2017 | Gao |
| 9,592,019 B2 | 3/2017 | Sugiyama |
| 9,805,507 B2 | 10/2017 | Chen |
| 9,808,215 B2 | 11/2017 | Ruth et al. |
| 9,811,758 B2 | 11/2017 | Ren et al. |
| 9,901,309 B2 | 2/2018 | DeFreitas et al. |
| 10,008,184 B2 | 6/2018 | Kreeger et al. |
| 10,010,302 B2 | 7/2018 | Ruth et al. |
| 10,074,199 B2 | 9/2018 | Robinson et al. |
| 10,092,358 B2 | 10/2018 | DeFreitas |
| 10,111,631 B2 | 10/2018 | Gkanatsios |
| 10,242,490 B2 | 3/2019 | Karssemeijer |
| 10,276,265 B2 | 4/2019 | Reicher et al. |
| 10,282,840 B2 | 5/2019 | Moehrle et al. |
| 10,335,094 B2 | 7/2019 | DeFreitas |
| 10,357,211 B2 | 7/2019 | Smith |
| 10,410,417 B2 | 9/2019 | Chen et al. |
| 10,413,263 B2 | 9/2019 | Ruth et al. |
| 10,444,960 B2 | 10/2019 | Marshall |
| 10,456,213 B2 | 10/2019 | DeFreitas |
| 10,573,276 B2 | 2/2020 | Kreeger et al. |
| 10,575,807 B2 | 3/2020 | Gkanatsios |
| 10,595,954 B2 | 3/2020 | DeFreitas |
| 10,624,598 B2 | 4/2020 | Chen |
| 10,977,863 B2 | 4/2021 | Chen |
| 10,978,026 B2 | 4/2021 | Kreeger |
| 11,419,565 B2 | 8/2022 | Gkanatsios |
| 11,508,340 B2 | 11/2022 | Kreeger |
| 11,701,199 B2 | 7/2023 | DeFreitas |
| 2001/0038681 A1 | 11/2001 | Stanton et al. |
| 2001/0038861 A1 | 11/2001 | Hsu et al. |
| 2002/0012450 A1 | 1/2002 | Tsuji |
| 2002/0050986 A1 | 5/2002 | Inoue |
| 2002/0075997 A1 | 6/2002 | Unger et al. |
| 2002/0113681 A1 | 8/2002 | Byram |
| 2002/0122533 A1 | 9/2002 | Marie et al. |
| 2002/0188466 A1 | 12/2002 | Barrette et al. |
| 2002/0193676 A1 | 12/2002 | Bodicker |
| 2003/0007598 A1 | 1/2003 | Wang |
| 2003/0018272 A1 | 1/2003 | Treado et al. |
| 2003/0026386 A1 | 2/2003 | Tang |
| 2003/0048260 A1 | 3/2003 | Matusis |
| 2003/0073895 A1 | 4/2003 | Nields et al. |
| 2003/0095624 A1 | 5/2003 | Eberhard et al. |
| 2003/0097055 A1 | 5/2003 | Yanof |
| 2003/0128893 A1 | 7/2003 | Castorina |
| 2003/0135115 A1 | 7/2003 | Burdette et al. |
| 2003/0169847 A1 | 9/2003 | Karellas |
| 2003/0194050 A1 | 10/2003 | Eberhard |
| 2003/0194121 A1 | 10/2003 | Eberhard et al. |
| 2003/0194124 A1 | 10/2003 | Suzuki et al. |
| 2003/0195433 A1 | 10/2003 | Turovskiy |
| 2003/0210254 A1 | 11/2003 | Doan |
| 2003/0212327 A1 | 11/2003 | Wang |
| 2003/0215120 A1 | 11/2003 | Uppaluri |
| 2004/0008809 A1 | 1/2004 | Webber |
| 2004/0008900 A1 | 1/2004 | Jabri et al. |
| 2004/0008901 A1 | 1/2004 | Avinash |
| 2004/0036680 A1 | 2/2004 | Davis |
| 2004/0047518 A1 | 3/2004 | Tiana |
| 2004/0052328 A1 | 3/2004 | Saboi |
| 2004/0064037 A1 | 4/2004 | Smith |
| 2004/0066884 A1 | 4/2004 | Claus |
| 2004/0066904 A1 | 4/2004 | Eberhard et al. |
| 2004/0070582 A1 | 4/2004 | Smith et al. |
| 2004/0077938 A1 | 4/2004 | Mark et al. |
| 2004/0081273 A1 | 4/2004 | Ning |
| 2004/0094167 A1 | 5/2004 | Brady |
| 2004/0101095 A1 | 5/2004 | Jing et al. |
| 2004/0109028 A1 | 6/2004 | Stern et al. |
| 2004/0109529 A1 | 6/2004 | Eberhard et al. |
| 2004/0127789 A1 | 7/2004 | Ogawa |
| 2004/0138569 A1 | 7/2004 | Grunwald |
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0047636 A1* | 3/2005 | Gines .................. G06T 11/005 378/4 |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0084060 A1 | 4/2005 | Seppi et al. |
| 2005/0089205 A1 | 4/2005 | Kapur |
| 2005/0105679 A1 | 5/2005 | Wu et al. |
| 2005/0107689 A1 | 5/2005 | Sasano |
| 2005/0111718 A1 | 5/2005 | MacMahon |
| 2005/0113680 A1 | 5/2005 | Ikeda et al. |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2005/0135555 A1 | 6/2005 | Claus |

(56) References Cited

U.S. PATENT DOCUMENTS

| | | |
|---|---|---|
| 2005/0135664 A1 | 6/2005 | Kaufhold |
| 2005/0226375 A1 | 10/2005 | Eberhard |
| 2006/0004278 A1 | 1/2006 | Giger et al. |
| 2006/0009693 A1 | 1/2006 | Hanover et al. |
| 2006/0018526 A1 | 1/2006 | Avinash |
| 2006/0025680 A1 | 2/2006 | Jeune-Iomme |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0132508 A1 | 6/2006 | Sadikali |
| 2006/0147099 A1 | 7/2006 | Marshall et al. |
| 2006/0154267 A1 | 7/2006 | Ma et al. |
| 2006/0155209 A1 | 7/2006 | Miller et al. |
| 2006/0197753 A1 | 9/2006 | Hotelling |
| 2006/0210131 A1 | 9/2006 | Wheeler |
| 2006/0228012 A1 | 10/2006 | Masuzawa |
| 2006/0238546 A1 | 10/2006 | Handley |
| 2006/0257009 A1 | 11/2006 | Wang |
| 2006/0269040 A1 | 11/2006 | Mertelmeier |
| 2006/0274928 A1 | 12/2006 | Collins et al. |
| 2006/0291618 A1 | 12/2006 | Eberhard et al. |
| 2007/0014468 A1 | 1/2007 | Gines et al. |
| 2007/0019846 A1 | 1/2007 | Bullitt et al. |
| 2007/0030949 A1 | 2/2007 | Jing et al. |
| 2007/0036265 A1 | 2/2007 | Jing et al. |
| 2007/0046649 A1 | 3/2007 | Reiner |
| 2007/0047793 A1 | 3/2007 | Wu et al. |
| 2007/0052700 A1 | 3/2007 | Wheeler et al. |
| 2007/0076844 A1 | 4/2007 | Defreitas et al. |
| 2007/0114424 A1 | 5/2007 | Danielsson et al. |
| 2007/0118400 A1 | 5/2007 | Morita et al. |
| 2007/0156451 A1 | 7/2007 | Gering |
| 2007/0223651 A1 | 9/2007 | Wagenaar et al. |
| 2007/0225600 A1 | 9/2007 | Weibrecht et al. |
| 2007/0236490 A1 | 10/2007 | Casteele |
| 2007/0242800 A1 | 10/2007 | Jing et al. |
| 2007/0263765 A1 | 11/2007 | Wu |
| 2007/0274585 A1 | 11/2007 | Zhang et al. |
| 2008/0019581 A1 | 1/2008 | Gkanatsios et al. |
| 2008/0043905 A1 | 2/2008 | Hassanpourgol |
| 2008/0045833 A1 | 2/2008 | DeFreitas et al. |
| 2008/0101537 A1 | 5/2008 | Sendai |
| 2008/0114614 A1 | 5/2008 | Mahesh et al. |
| 2008/0125643 A1 | 5/2008 | Huisman |
| 2008/0130979 A1 | 6/2008 | Ren |
| 2008/0139896 A1 | 6/2008 | Baumgart |
| 2008/0152086 A1 | 6/2008 | Hall |
| 2008/0165136 A1 | 7/2008 | Christie et al. |
| 2008/0187095 A1 | 8/2008 | Boone et al. |
| 2008/0198966 A1 | 8/2008 | Hjarn |
| 2008/0221479 A1 | 9/2008 | Ritchie |
| 2008/0229256 A1 | 9/2008 | Shibaike |
| 2008/0240533 A1 | 10/2008 | Piron et al. |
| 2008/0297482 A1 | 12/2008 | Weiss |
| 2009/0003519 A1 | 1/2009 | DeFreitas et al. |
| 2009/0005668 A1 | 1/2009 | West et al. |
| 2009/0005693 A1 | 1/2009 | Brauner |
| 2009/0010384 A1 | 1/2009 | Jing et al. |
| 2009/0034684 A1 | 2/2009 | Bernard |
| 2009/0037821 A1 | 2/2009 | O'Neal et al. |
| 2009/0063118 A1* | 3/2009 | Dachille ............... G06T 7/0012 703/11 |
| 2009/0079705 A1 | 3/2009 | Sizelove et al. |
| 2009/0080594 A1 | 3/2009 | Brooks et al. |
| 2009/0080602 A1 | 3/2009 | Brooks et al. |
| 2009/0080604 A1 | 3/2009 | Shores et al. |
| 2009/0080752 A1 | 3/2009 | Ruth |
| 2009/0080765 A1 | 3/2009 | Bernard et al. |
| 2009/0087067 A1 | 4/2009 | Khorasani |
| 2009/0123052 A1 | 5/2009 | Ruth |
| 2009/0129644 A1 | 5/2009 | Daw et al. |
| 2009/0135997 A1 | 5/2009 | Defreitas et al. |
| 2009/0138280 A1 | 5/2009 | Morita et al. |
| 2009/0143674 A1 | 6/2009 | Nields |
| 2009/0167702 A1 | 7/2009 | Nurmi |
| 2009/0171244 A1 | 7/2009 | Ning |
| 2009/0238424 A1 | 9/2009 | Arakita |
| 2009/0259958 A1 | 10/2009 | Ban |
| 2009/0268865 A1 | 10/2009 | Ren et al. |
| 2009/0278812 A1 | 11/2009 | Yasutake |
| 2009/0296882 A1 | 12/2009 | Gkanatsios et al. |
| 2009/0304147 A1 | 12/2009 | Jing et al. |
| 2010/0034348 A1 | 2/2010 | Yu |
| 2010/0049046 A1 | 2/2010 | Peiffer |
| 2010/0054400 A1 | 3/2010 | Ren et al. |
| 2010/0067648 A1 | 3/2010 | Kojima |
| 2010/0079405 A1 | 4/2010 | Bernstein |
| 2010/0086188 A1 | 4/2010 | Ruth et al. |
| 2010/0088346 A1 | 4/2010 | Urness et al. |
| 2010/0098214 A1 | 4/2010 | Star-Lack et al. |
| 2010/0105879 A1 | 4/2010 | Katayose et al. |
| 2010/0121178 A1 | 5/2010 | Krishnan |
| 2010/0131294 A1 | 5/2010 | Venon |
| 2010/0131482 A1 | 5/2010 | Linthicum et al. |
| 2010/0135558 A1 | 6/2010 | Ruth et al. |
| 2010/0152570 A1 | 6/2010 | Navab |
| 2010/0166147 A1 | 7/2010 | Abenaim |
| 2010/0166267 A1 | 7/2010 | Zhang |
| 2010/0171764 A1* | 7/2010 | Feng ..................... G06V 10/25 345/660 |
| 2010/0189322 A1* | 7/2010 | Sakagawa ............. G16H 30/40 382/128 |
| 2010/0195882 A1 | 8/2010 | Ren et al. |
| 2010/0208037 A1 | 8/2010 | Sendai |
| 2010/0231522 A1 | 9/2010 | Li |
| 2010/0246884 A1 | 9/2010 | Chen et al. |
| 2010/0246909 A1 | 9/2010 | Blum |
| 2010/0259561 A1 | 10/2010 | Forutanpour et al. |
| 2010/0259645 A1 | 10/2010 | Kaplan |
| 2010/0260316 A1 | 10/2010 | Stein et al. |
| 2010/0280375 A1 | 11/2010 | Zhang |
| 2010/0293500 A1 | 11/2010 | Cragun |
| 2011/0018817 A1 | 1/2011 | Kryze |
| 2011/0019891 A1 | 1/2011 | Puong |
| 2011/0054944 A1 | 3/2011 | Sandberg et al. |
| 2011/0069808 A1 | 3/2011 | Defreitas et al. |
| 2011/0069906 A1 | 3/2011 | Park |
| 2011/0087132 A1 | 4/2011 | DeFreitas et al. |
| 2011/0105879 A1 | 5/2011 | Masumoto |
| 2011/0109650 A1 | 5/2011 | Kreeger |
| 2011/0110570 A1 | 5/2011 | Bar-Shalev |
| 2011/0110576 A1 | 5/2011 | Kreeger |
| 2011/0123073 A1 | 5/2011 | Gustafson |
| 2011/0125526 A1 | 5/2011 | Gustafson |
| 2011/0134113 A1 | 6/2011 | Ma et al. |
| 2011/0150447 A1 | 6/2011 | Li |
| 2011/0157154 A1* | 6/2011 | Bernard ............... A61B 6/5229 345/419 |
| 2011/0163939 A1 | 7/2011 | Tam et al. |
| 2011/0178389 A1 | 7/2011 | Kumar et al. |
| 2011/0182402 A1 | 7/2011 | Partain |
| 2011/0234630 A1 | 9/2011 | Batman et al. |
| 2011/0237927 A1 | 9/2011 | Brooks et al. |
| 2011/0242092 A1 | 10/2011 | Kashiwagi |
| 2011/0310126 A1 | 12/2011 | Georgiev et al. |
| 2012/0014501 A1 | 1/2012 | Pelc |
| 2012/0014504 A1 | 1/2012 | Jang |
| 2012/0014578 A1* | 1/2012 | Karssemeijer ........ G06T 7/0012 382/131 |
| 2012/0069951 A1 | 3/2012 | Toba |
| 2012/0106698 A1 | 5/2012 | Karim |
| 2012/0127297 A1 | 5/2012 | Baxi |
| 2012/0131488 A1 | 5/2012 | Karlsson et al. |
| 2012/0133600 A1 | 5/2012 | Marshall |
| 2012/0133601 A1 | 5/2012 | Marshall |
| 2012/0134464 A1 | 5/2012 | Hoernig et al. |
| 2012/0148151 A1 | 6/2012 | Hamada |
| 2012/0150034 A1 | 6/2012 | DeFreitas et al. |
| 2012/0189092 A1 | 7/2012 | Jerebko |
| 2012/0194425 A1 | 8/2012 | Buelow |
| 2012/0238870 A1 | 9/2012 | Smith et al. |
| 2012/0277625 A1 | 11/2012 | Nakayama |
| 2012/0293511 A1 | 11/2012 | Mertelmeier |

(56) References Cited

U.S. PATENT DOCUMENTS

| | | | |
|---|---|---|---|
| 2013/0016255 A1* | 1/2013 | Bhatt | G06T 3/40 |
| | | | 348/240.2 |
| 2013/0022165 A1 | 1/2013 | Jang | |
| 2013/0044861 A1 | 2/2013 | Muller | |
| 2013/0059758 A1 | 3/2013 | Haick | |
| 2013/0108138 A1 | 5/2013 | Nakayama | |
| 2013/0121569 A1 | 5/2013 | Yadav | |
| 2013/0121618 A1 | 5/2013 | Yadav | |
| 2013/0202168 A1 | 8/2013 | Jerebko | |
| 2013/0259193 A1 | 10/2013 | Packard | |
| 2013/0272494 A1 | 10/2013 | DeFreitas | |
| 2014/0033126 A1 | 1/2014 | Kreeger | |
| 2014/0035811 A1 | 2/2014 | Guehring | |
| 2014/0064444 A1 | 3/2014 | Oh | |
| 2014/0073913 A1 | 3/2014 | DeFreitas et al. | |
| 2014/0082542 A1* | 3/2014 | Zhang | G16H 30/40 |
| | | | 715/771 |
| 2014/0200433 A1 | 7/2014 | Choi | |
| 2014/0219534 A1 | 8/2014 | Wiemker et al. | |
| 2014/0219548 A1 | 8/2014 | Wels | |
| 2014/0276061 A1 | 9/2014 | Lee et al. | |
| 2014/0327702 A1 | 11/2014 | Kreeger et al. | |
| 2014/0328517 A1 | 11/2014 | Gluncic | |
| 2015/0004558 A1 | 1/2015 | Inglese | |
| 2015/0052471 A1 | 2/2015 | Chen | |
| 2015/0061582 A1 | 4/2015 | Smith | |
| 2015/0238148 A1 | 8/2015 | Georgescu | |
| 2015/0258271 A1 | 9/2015 | Love | |
| 2015/0302146 A1 | 10/2015 | Marshall | |
| 2015/0309712 A1 | 10/2015 | Marshall | |
| 2015/0317538 A1 | 11/2015 | Ren et al. | |
| 2015/0331995 A1 | 11/2015 | Zhao | |
| 2016/0000399 A1 | 1/2016 | Halmann et al. | |
| 2016/0022364 A1 | 1/2016 | DeFreitas et al. | |
| 2016/0051215 A1 | 2/2016 | Chen | |
| 2016/0078645 A1 | 3/2016 | Abdurahman | |
| 2016/0140749 A1 | 5/2016 | Erhard | |
| 2016/0210774 A1 | 7/2016 | Wiskin et al. | |
| 2016/0228034 A1 | 8/2016 | Gluncic | |
| 2016/0235380 A1 | 8/2016 | Smith | |
| 2016/0350933 A1 | 12/2016 | Schieke | |
| 2016/0364526 A1 | 12/2016 | Reicher et al. | |
| 2016/0367210 A1 | 12/2016 | Gkanatsios | |
| 2017/0071562 A1 | 3/2017 | Suzuki | |
| 2017/0132792 A1 | 5/2017 | Jerebko et al. | |
| 2017/0202453 A1* | 7/2017 | Sekiguchi | G06T 11/003 |
| 2017/0262737 A1 | 9/2017 | Rabinovich | |
| 2018/0008220 A1 | 1/2018 | Boone et al. | |
| 2018/0008236 A1 | 1/2018 | Venkataraman et al. | |
| 2018/0047211 A1 | 2/2018 | Chen et al. | |
| 2018/0109698 A1 | 4/2018 | Ramsay et al. | |
| 2018/0132722 A1 | 5/2018 | Eggers et al. | |
| 2018/0137385 A1 | 5/2018 | Ren | |
| 2018/0144244 A1 | 5/2018 | Masoud | |
| 2018/0256118 A1 | 9/2018 | DeFreitas | |
| 2019/0000318 A1 | 1/2019 | Caluser | |
| 2019/0015173 A1 | 1/2019 | DeFreitas | |
| 2019/0037173 A1* | 1/2019 | Lee | G06F 3/04842 |
| 2019/0043456 A1 | 2/2019 | Kreeger | |
| 2019/0057778 A1 | 2/2019 | Porter et al. | |
| 2019/0287241 A1 | 9/2019 | Hill et al. | |
| 2019/0290221 A1 | 9/2019 | Smith | |
| 2019/0325573 A1* | 10/2019 | Bernard | A61B 6/469 |
| 2020/0046303 A1 | 2/2020 | DeFreitas | |
| 2020/0054300 A1* | 2/2020 | Kreeger | G06T 11/003 |
| 2020/0093562 A1 | 3/2020 | DeFreitas | |
| 2020/0184262 A1 | 6/2020 | Chui | |
| 2020/0205928 A1 | 7/2020 | DeFreitas | |
| 2020/0253573 A1 | 8/2020 | Gkanatsios | |
| 2020/0345320 A1 | 11/2020 | Chen | |
| 2020/0390404 A1 | 12/2020 | DeFreitas | |
| 2021/0000553 A1 | 1/2021 | St. Pierre | |
| 2021/0100518 A1 | 4/2021 | Chui | |
| 2021/0100626 A1 | 4/2021 | St. Pierre | |
| 2021/0113167 A1 | 4/2021 | Chui | |
| 2021/0118199 A1 | 4/2021 | Chui | |
| 2021/0174504 A1 | 6/2021 | Madabhushi | |
| 2021/0212665 A1 | 7/2021 | Tsymbalenko | |
| 2022/0005277 A1 | 1/2022 | Chen | |
| 2022/0013089 A1 | 1/2022 | Kreeger | |
| 2022/0036545 A1 | 2/2022 | St. Pierre | |
| 2022/0192615 A1 | 6/2022 | Chui | |
| 2022/0254023 A1* | 8/2022 | McKinney | G06F 18/24133 |
| 2022/0386969 A1 | 12/2022 | Smith | |
| 2023/0000467 A1 | 1/2023 | Shi | |
| 2023/0033601 A1 | 2/2023 | Chui | |
| 2023/0038498 A1 | 2/2023 | Xu | |
| 2023/0053489 A1 | 2/2023 | Kreeger | |
| 2023/0054121 A1 | 2/2023 | Chui | |
| 2023/0056692 A1 | 2/2023 | Gkanatsios | |
| 2023/0082494 A1 | 3/2023 | Chui | |
| 2023/0098305 A1 | 3/2023 | St. Pierre | |
| 2023/0103969 A1 | 4/2023 | St. Pierre | |
| 2023/0124481 A1 | 4/2023 | St. Pierre | |
| 2023/0225821 A1 | 7/2023 | DeFreitas | |
| 2023/0344453 A1 | 10/2023 | Yang | |
| 2024/0169958 A1 | 5/2024 | Kreeger | |
| 2024/0315654 A1 | 9/2024 | Chui | |
| 2024/0320827 A1 | 9/2024 | Chui | |

FOREIGN PATENT DOCUMENTS

| | | |
|---|---|---|
| CN | 1846662 | 10/2006 |
| CN | 101066212 A | 11/2007 |
| CN | 102169530 A | 8/2011 |
| CN | 202161328 | 3/2012 |
| CN | 102429678 | 5/2012 |
| CN | 102473300 A | 5/2012 |
| CN | 105193447 | 12/2015 |
| CN | 106659468 A | 5/2017 |
| CN | 107440730 | 12/2017 |
| CN | 112561908 A | 3/2021 |
| DE | 102010009295 | 8/2011 |
| DE | 102011087127 | 5/2013 |
| EP | 775467 | 5/1997 |
| EP | 928001 | 3/2000 |
| EP | 1428473 | 6/2004 |
| EP | 2236085 | 6/2010 |
| EP | 2215600 | 8/2010 |
| EP | 2301432 | 3/2011 |
| EP | 2491863 | 8/2012 |
| EP | 1986548 | 1/2013 |
| EP | 2656789 | 10/2013 |
| EP | 2823464 | 1/2015 |
| EP | 2823765 | 1/2015 |
| EP | 2889743 | 7/2015 |
| EP | 3060132 | 4/2019 |
| JP | H09-35043 | 2/1997 |
| JP | H09-198490 | 7/1997 |
| JP | H09-238934 | 9/1997 |
| JP | H10-33523 | 2/1998 |
| JP | 2000-200340 | 7/2000 |
| JP | 2002-109510 | 4/2002 |
| JP | 2002-282248 | 10/2002 |
| JP | 2003-126073 | 5/2003 |
| JP | 2003-189179 | 7/2003 |
| JP | 2003-199737 | 7/2003 |
| JP | 2003-531516 | 10/2003 |
| JP | 2004254742 | 9/2004 |
| JP | 2005-110843 | 4/2005 |
| JP | 2005-522305 | 7/2005 |
| JP | 2005-227350 | 8/2005 |
| JP | 2005-322257 | 11/2005 |
| JP | 2006-519634 | 8/2006 |
| JP | 2006-312026 | 11/2006 |
| JP | 2007-130487 | 5/2007 |
| JP | 2007-216022 | 8/2007 |
| JP | 2007-325928 | 12/2007 |
| JP | 2007-330334 | 12/2007 |
| JP | 2007-536968 | 12/2007 |
| JP | 2008-068032 | 3/2008 |
| JP | 2008518684 | 6/2008 |
| JP | 2008-253401 | 10/2008 |
| JP | 2009-034503 | 2/2009 |

(56) References Cited

FOREIGN PATENT DOCUMENTS

| | | |
|---|---|---|
| JP | 2009-522005 | 6/2009 |
| JP | 2009-526618 | 7/2009 |
| JP | 2009-207545 | 9/2009 |
| JP | 2010-137004 | 6/2010 |
| JP | 2011-110175 A | 6/2011 |
| JP | 2012-011255 | 1/2012 |
| JP | 2012-501750 | 1/2012 |
| JP | 2012-061196 | 3/2012 |
| JP | 2013-530768 | 8/2013 |
| JP | 2013-244211 | 12/2013 |
| JP | 2014-507250 | 3/2014 |
| JP | 2014-534042 | 12/2014 |
| JP | 2015-506794 | 3/2015 |
| JP | 2015-144632 A | 8/2015 |
| JP | 2016-198197 | 12/2015 |
| JP | 2016059743 | 4/2016 |
| JP | 2017-000364 | 1/2017 |
| JP | 2017-056358 | 3/2017 |
| KR | 10-2015-0010515 | 1/2015 |
| KR | 10-2017-0062839 | 6/2017 |
| WO | 90/05485 | 5/1990 |
| WO | 93/17620 | 9/1993 |
| WO | 94/06352 | 3/1994 |
| WO | 1997/00649 | 1/1997 |
| WO | 1998/16903 | 4/1998 |
| WO | 00/51484 | 9/2000 |
| WO | 2003/020114 | 3/2003 |
| WO | 03/077202 | 9/2003 |
| WO | 2005051197 | 6/2005 |
| WO | 2005110230 | 11/2005 |
| WO | 2005112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008047270 | 4/2008 |
| WO | 2008/050823 | 5/2008 |
| WO | 2008/054436 | 5/2008 |
| WO | 2009/026587 | 2/2009 |
| WO | 2010/028208 | 3/2010 |
| WO | 2010059920 | 5/2010 |
| WO | 2011008239 | 1/2011 |
| WO | 2011/043838 | 4/2011 |
| WO | 2011065950 | 6/2011 |
| WO | 2011073864 | 6/2011 |
| WO | 2011091300 | 7/2011 |
| WO | 2012/001572 | 1/2012 |
| WO | 2012/068373 | 5/2012 |
| WO | 2012063653 | 5/2012 |
| WO | 2012/112627 | 8/2012 |
| WO | 2012/122399 | 9/2012 |
| WO | 2013/001439 | 1/2013 |
| WO | 2013/035026 | 3/2013 |
| WO | 2013/078476 | 5/2013 |
| WO | 2013/123091 | 8/2013 |
| WO | 2013/136222 | 9/2013 |
| WO | 2014/080215 | 5/2014 |
| WO | 2014/149554 | 9/2014 |
| WO | 2014/207080 | 12/2014 |
| WO | 2015/061582 | 4/2015 |
| WO | 2015/066650 | 5/2015 |
| WO | 2015/130916 | 9/2015 |
| WO | 2016/103094 | 6/2016 |
| WO | 2016/184746 | 11/2016 |
| WO | 2016/206942 | 12/2016 |
| WO | 2018/183548 | 10/2018 |
| WO | 2018/183549 | 10/2018 |
| WO | 2018/183550 | 10/2018 |
| WO | 2018/236565 | 12/2018 |
| WO | 2019/032558 | 2/2019 |
| WO | 2019/091807 | 5/2019 |
| WO | 2021/021329 | 2/2021 |
| WO | 2021/168281 | 8/2021 |
| WO | 2021/195084 | 9/2021 |

OTHER PUBLICATIONS

Duan, Xiaoman et al., "Matching corresponding regions of interest on cranio-caudal and medio-lateral oblique view mammograms", IEEE Access, vol. 7, Mar. 25, 2019, pp. 31586-31597, XP011715754, DOI: 10.1109/Access.2019.2902854, retrieved on Mar. 20, 2019, abstract.

Samulski, Maurice et al., "Optimizing case-based detection performance in a multiview CAD system for mammography", IEEE Transactions on Medical Imaging, vol. 30, No. 4, Apr. 1, 2011, pp. 1001-1009, XP011352387, ISSN: 0278-0062, DOI: 10.1109/TMI.2011.2105886, abstract.

Nikunjc, Oza et al., Dietterich, T.G., Ed., "Ensemble methods in machine learning", Jan. 1, 2005, Multiple Classifier Systems, Lecture Notes in Computer Science; LNCS, Springer-Verlag Berlin/Heidelberg, pp. 1-15, abstract.

"Filtered Back Projection", (NYGREN), published May 8, 2007, URL: http://web.archive.org/web/19991010131715/http://www.owlnet.rice.edu/~elec539/Projects97/cult/node2.html, 2 pgs.

"Supersonic to feature Aixplorer Ultimate at ECR", AuntiMinnie.com, 3 pages (Feb. 2018).

Al Sallab et al., "Self Learning Machines Using Deep Networks", Soft Computing and Pattern Recognition (SoCPaR), 2011 Int'l. Conference of IEEE, Oct. 14, 2011, pp. 21-26.

Berg, WA et al., "Combined screening with ultrasound and mammography vs mammography alone in women at elevated risk of breast cancer", JAMA 299:2151-2163, 2008.

Burbank, Fred, "Stereotactic Breast Biopsy: Its History, Its Present, and Its Future", published in 1996 at the Southeastern Surgical Congress, 24 pages.

Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.

Caroline, B.E. et al., "Computer aided detection of masses in digital breast tomosynthesis: A review", 2012 International Conference on Emerging Trends in Science, Engineering and Technology (INCOSET), Tiruchirappalli, 2012, pp. 186-191.

Carton, AK, et al., "Dual-energy contrast-enhanced digital breast tomosynthesis—a feasibility study", BR J Radiol. Apr. 2010;83(988):344-50.

Chan, Heang-Ping et al., "Computer-aided detection system for breast masses on digital tomosynthesis mammograms: Preliminary Experience", Radiology, Dec. 2005, 1075-1080.

Chan, Heang-Ping et al., "ROC Study of the effect of stereoscopic imaging on assessment of breast lesions," Medical Physics, vol. 32, No. 4, Apr. 2005, 1001-1009.

Chen, SC, et al., "Initial clinical experience with contrast-enhanced digital breast tomosynthesis", Acad Radio. Feb. 2007 14(2):229-38.

Conner, Peter, "Breast Response to Menopausal Hormone Therapy—Aspects on Proliferation, apoptosis and Mammographic Density", 2007 Annals of Medicine, 39;1, 28-41.

Diekmann, Felix et al., "Thick Slices from Tomosynthesis Data Sets: Phantom Study for the Evaluation of Different Algorithms", Journal of Digital Imaging, Springer, vol. 22, No. 5, Oct. 23, 2007, pp. 519-526.

Diekmann, Felix., et al., "Digital mammography using iodine-based contrast media: initial clinical experience with dynamic contrast medium enhancement", Invest Radiol 2005; 40:397-404.

Dromain C., et al., "Contrast enhanced spectral mammography: a multi-reader study", RSNA 2010, 96th Scientific Assembly and Scientific Meeting.

Dromain, C., et al., "Contrast-enhanced digital mammography", Eur J Radiol. 2009; 69:34-42.

Dromain, Clarisse et al., "Dual-energy contrast-enhanced digital mammography: initial clinical results", European Radiology, Sep. 14, 2010, vol. 21, pp. 565-574.

Dromain, Clarisse, et al., "Evaluation of tumor angiogenesis of breast carcinoma using contrast-enhanced digital mammography", AJR: 187, Nov. 2006, 16 pages.

E. Shaw de Paredes et al., "Interventional Breast Procedure", published Sep./Oct. 1998 in Curr Probl Diagn Radiol, pp. 138-184.

(56) References Cited

OTHER PUBLICATIONS

EFilm Mobile HD by Merge Healthcare, web site: http://itunes.apple.com/bw/app/efilm-mobile-hd/id405261243?mt=8, accessed on Nov. 3, 2011 (2 pages).

EFilm Solutions, eFilm Workstation (tm) 3.4, website: http://estore.merge.com/na/estore/content.aspx?productID=405, accessed on Nov. 3, 2011 (2 pages).

Elbakri, Idris A. et al., "Automatic exposure control for a slot scanning full field digital mammography system", Med. Phys. 2005; Sep. 32(9):2763-2770, Abstract only.

Ertas, M. et al., "2D versus 3D total variation minimization in digital breast tomosynthesis", 2015 IEEE International Conference on Imaging Systems and Techniques (IST), Macau, 2015, pp. 1-4.

Feng, Steve Si Jia, et al., "Clinical digital breast tomosynthesis system: Dosimetric Characterization", Radiology, Apr. 2012, 263(1); pp. 35-42.

Fischer Imaging Corp, Mammotest Plus manual on minimally invasive breast biopsy system, 2002, 8 pages.

Fischer Imaging Corporation, Installation Manual, MammoTest Family of Breast Biopsy Systems, 86683G, 86684G, P-55957-IM, Issue 1, Revision 3, Jul. 2005, 98 pages.

Fischer Imaging Corporation, Operator Manual, MammoTest Family of Breast Biopsy Systems, 86683G, 86684G, P-55956-OM, Issue 1, Revision 6, Sep. 2005, 258 pages.

Freiherr, G., "Breast tomosynthesis trials show promise", Diagnostic Imaging—San Francisco 2005, V27; N4:42-48.

Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages.

Ghiassi, M. et al., "A Dynamic Architecture for Artificial Networks", Neurocomputing, vol. 63, Aug. 20, 2004, pp. 397-413.

Giger et al. "Development of a smart workstation for use in mammography", in Proceedings of SPIE, vol. 1445 (1991), pp. 101103; 4 pages.

Giger et al., "An Intelligent Workstation for Computer-aided Diagnosis", in RadioGraphics, May 1993, 13:3 pp. 647-656; 10 pages.

Glick, Stephen J., "Breast CT", Annual Rev. Biomed. Eng., Sep. 2007;501-26.

Hologic, "Lorad StereoLoc II" Operator's Manual 9-500-0261, Rev. 005, 2004, 78 pgs.

Hologic, Inc., 510(k) Summary, prepared Nov. 28, 2010, for Affirm Breast Biopsy Guidance System Special 510(k) Premarket Notification, 5 pages.

Hologic, Inc., 510(k) Summary, prepared Aug. 14, 2012, for Affirm Breast Biopsy Guidance System Special 510(k) Premarket Notification, 5 pages.

ICRP Publication 60: 1990 Recommendations of the International Commission on Radiological Protection, 12 pages.

Ijaz, Umer Zeeshan, et al., "Mammography phantom studies using 3D electrical impedance tomography with numerical forward solver", Frontiers in the Convergence of Bioscience and Information Technologies 2007, 379-383.

Jochelson, M., et al., "Bilateral Dual Energy contrast-enhanced digital mammography: Initial Experience", RSNA 2010, 96th Scientific Assembly and Scientific Meeting. 1 page.

Jong, RA, et al., Contrast-enhanced digital mammography: initial clinical experience. Radiology 2003; 228:842-850.

Kao, Tzu-Jen et al., "Regional admittivity spectra with tomosynthesis images for breast cancer detection", Proc. Of the 29th Annual Int'l. Conf. of the IEEE EMBS, Aug. 23-26, 2007, 4142-4145.

Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009.

Kopans, Daniel B., "Breast Imaging", 3rd Edition, Lippincott Williams and Wilkins, published Nov. 2, 2006, pp. 960-967.

Kopans, et al. Will tomosynthesis replace conventional mammography? Plenary Session SFN08: RSNA 2005.

Lehman, CD, et al. MRI evaluation of the contralateral breast in women with recently diagnosed breast cancer. N Engl J Med 2007; 356:1295-1303.

Lewin, JM, et al., Dual-energy contrast-enhanced digital subtraction mammography: feasibility. Radiology 2003; 229:261-268.

Lilja, Mikko, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway, NJ, Oct. 25, 2008.

Lindfors, KK, et al., Dedicated breast CT: initial clinical experience. Radiology 2008; 246(3): 725-733.

Mahesh, Mahadevappa, "AAPM/RSNA Physics Tutorial for Residents—Digital Mammography: An Overview", Nov.-Dec. 2004, vol. 24, No. 6, 1747-1760.

Metheany, Kathrine G. et al., "Characterizing anatomical variability in breast CT images", Oct. 2008, Med. Phys. 35 (10); 4685-4694.

Niklason, L., et al., Digital tomosynthesis in breast imaging. Radiology. Nov. 1997; 205(2):399-406.

Pathmanathan et al., "Predicting tumour location by simulating large deformations of the breast using a 3D finite element model and nonlinear elasticity", Medical Image Computing and Computer-Assisted Intervention, pp. 217-224, vol. 3217 (2004).

Pediconi, "Color-coded automated signal intensity-curve for detection and characterization of breast lesions: Preliminary evaluation of new software for MR-based breast imaging," International Congress Series 1281 (2005) 1081-1086.

Poplack, SP, et al., Digital breast tomosynthesis: initial experience in 98 women with abnormal digital screening mammography. AJR Am J Roentgenology Sep. 2007 189(3):616-23.

Prionas, ND, et al., Contrast-enhanced dedicated breast CT: initial clinical experience. Radiology. Sep. 2010 256(3):714-723.

Rafferty, E. et al., "Assessing Radiologist Performance Using Combined Full-Field Digital Mammography and Breast Tomosynthesis Versus Full-Field Digital Mammography Alone: Results" . . . presented at 2007 Radiological Society of North America meeting, Chicago IL.

Reynolds, April, "Stereotactic Breast Biopsy: A Review", Radiologic Technology, vol. 80, No. 5, Jun. 1, 2009, pp. 447M-464M, XP055790574.

Sakic et al., "Mammogram synthesis using a 3D simulation. I. breast tissue model and image acquisition simulation" Medical Physics. 29, pp. 2131-2139 (2002).

Samani, A. et al., "Biomechanical 3-D Finite Element Modeling of the Human Breast Using MRI Data", 2001, IEEE Transactions on Medical Imaging, vol. 20, No. 4, pp. 271-279.

Sechopoulos, et al., "Glandular radiation dose in tomosynthesis of the breast using tungsten targets", Journal of Applied Clinical Medical Physics, vol. 8, No. 4, Fall 2008, 161-171.

Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.

Smith, A., "Full field breast tomosynthesis", Radiol Manage. Sep.-Oct. 2005; 27(5):25-31.

Taghibakhsh, F. et al., "High dynamic range 2-TFT amplified pixel sensor architecture for digital mammography tomosynthesis", IET Circuits Devices Syst., 2007, 1(10, pp. 87-92.

Van Schie, Guido, et al., "Generating Synthetic Mammograms from Reconstructed Tomosynthesis Volumes", IEEE Transactions on Medical Imaging, vol. 32, No. 12, Dec. 2013, 2322-2331.

Van Schie, Guido, et al., "Mass detection in reconstructed digital breast tomosynthesis volumes with a computer-aided detection system trained on 2D mammograms", Med. Phys. 40(4), Apr. 2013, 41902-1-41902-11.

Varjonen, Mari, "Three-Dimensional Digital Breast Tomosynthesis in the Early Diagnosis and Detection of Breast Cancer", IWDM 2006, LNCS 4046, 152-159.

Weidner N, et al., "Tumor angiogenesis and metastasis: correlation in invasive breast carcinoma", New England Journal of Medicine 1991; 324:1-8.

(56) References Cited

OTHER PUBLICATIONS

Weidner, N, "The importance of tumor angiogenesis: the evidence continues to grow", AM J Clin Pathol. Nov. 2004 122(5):696-703.

Wen, Junhai et al., "A study on truncated cone-beam sampling strategies for 3D mammography", 2004, IEEE, 3200-3204.

Williams, Mark B. et al., "Optimization of exposure parameters in full field digital mammography", Medical Physics 35, 2414 (May 20, 2008); doi: 10.1118/1.2912177, pp. 2414-2423.

Wodajo, Felasfa, MD, "Now Playing: Radiology Images from Your Hospital PACS on your iPad," Mar. 17, 2010; web site: http://www.imedicalapps.com/2010/03/now-playing-radiology-images-from-your-hospital-pacs-on-your-ipad/, accessed on Nov. 3, 2011 (3 pages).

Yin, H.M., et al., "Image Parser: a tool for finite element generation from three-dimensional medical images", BioMedical Engineering Online. 3:31, pp. 1-9, Oct. 1, 2004.

Zhang, Yiheng et al., "A comparative study of limited-angle cone-beam reconstruction methods for breast tomosythesis", Med Phys., Oct. 2006, 33(10): 3781-3795.

Zhao, Bo, et al., "Imaging performance of an amorphous selenium digital mammography detector in a breast tomosynthesis system", May 2008, Med. Phys 35(5); 1978-1987.

Cho, N. et al., "Distinguishing Benign from Malignant Masses at Breast US: Combined US Elastography and Color Doppler US-Influence on Radiologist Accuracy", Radiology, 262(1): 80-90 (Jan. 2012).

Green, C. et al., "Deformable mapping using biochemical models to relate corresponding lesions in digital breast tomosynthesis and automated breast ultrasound images", Medical Image Analysis, 60: 1-18 (Nov. 2019).

Kim, Eun Sil, et al., "Significance of microvascular evaluation of ductal lesions on breast ultrasonography: Influence on diagnostic performance", Clinical Imaging, Elsevier, NY, vol. 51, Jun. 6, 2018, pp. 252-259.

Lee, E. et al., "Combination of Quantitative Parameters of Shear Wave Elastography and Superb Microvascular Imaging to Evaluate Breast Masses", Korean Journal of Radiology: Official Journal of the Korean Radiological Society, 21(9): 1045-1054 (Jan. 2020).

Love, Susan M., et al. "Anatomy of the nipple and breast ducts revisited", Cancer, American Cancer Society, Philadelphia, PA, vol. 101, No. 9, Sep. 20, 2004, pp. 1947-1957.

* cited by examiner

AUTO-FOCUS TOOL FOR MULTIMODALITY IMAGE REVIEW

CROSS-REFERENCE TO RELATED APPLICATION(S)

This application claims the benefit of priority to U.S. Provisional Application No. 63/271,339, filed Oct. 25, 2021, which application is hereby incorporated in its entirety by reference.

BACKGROUND

An ongoing tension is found in today's healthcare environments, such as radiology departments, between providing high-quality image review and maintaining adequate patient throughput to keep costs under control. Despite ongoing advances in imaging technology and related data processing systems, it is the radiologist who continues to bear the burden of the cost-quality tradeoff. As used herein, radiologist generically refers to a medical professional that analyzes medical images and makes clinical determinations therefrom.

Radiologists have expressed a clinical need for an automated solution to correlate corresponding regions of interests (ROIs) in medical images acquired from various imaging modalities. ROIs may be associated with breast abnormalities such as masses or microcalcification. ROIs could also be associated with specific focus areas of the breast that radiologist are interested reviewing in more detail. For any given patient, a radiologist may be able to review images from mammography, ultrasound, and MRI of the same patient. In an effort to determine the location of the ROI in each image, the radiologist will make a visual comparison, sometimes aided by a separate ruler or simply using the radiologist's hand or fingers. If these areas of interest appear in multiple images, it may lead to the conclusion that the region of interest is indeed a mass or microcalcification. If, on the other hand, there is no distinct region of interest in the second image at the appropriate location, it may lead to a conclusion that the region of interest in the first image is not a mass or microcalcification. Previously presented automated solutions have been proposed to provide for correlation between images of different modalities. However, such solutions proved unsatisfactory due to the vast amount of training data required to train machine learning (ML) mechanisms and the inaccuracy of the results provided by those ML mechanisms. In addition, ML mechanisms involve a substantial amount of processing resources and the automated correlation have resulted in a delay in presenting images to the radiologists. As a result, healthcare professionals have been forced to perform the ROI correlations manually with the aid of image manipulation tools, such as pan and zoom tools. This manual ROI correlation results in excessive mouse clicks and movements that impede image review workflow, add review time and associated costs, and cause fatigue to the radiologist.

It is with respect to these and other general considerations that the aspects disclosed herein have been made. Also, although relatively specific problems may be discussed, it should be understood that the examples should not be limited to solving the specific problems identified in the background or elsewhere in the present disclosure.

SUMMARY

Examples of the present disclosure describe systems and methods for an auto-focus tool for multimodality image review. In aspects, an image review system may provide for the display of a set of medical images representing one or more imaging modalities. The system may also provide an auto-focus tool that may be used during the review of the set of medical images. After receiving an instruction to activate the auto-focus tool, the system may receive a selection of an ROI in at least one of the images in the set of medical images. The auto-focus tool may identify the location of the ROI within the image and use the identified ROI location to identify a corresponding area or ROI in the remaining set of medical images. The auto-focus tool may orient (e.g., pan, zoom, flip, rotate, align, center) and display the remaining set of medical images such that the identified area or ROI is prominently displayed in the set of medical images.

In one aspect, examples provided in the present disclosure relate to a system comprising: a processor; and memory coupled to the processor, the memory comprising computer executable instructions that, when executed, perform a method. The method comprises receiving a selection of a region of interest (ROI) in a first image of a plurality of images; identifying, using an auto-focus tool, a location of the ROI within the first image; identifying, using the auto-focus tool, an area corresponding to the location of the ROI in at least a second image of the plurality of images, wherein the first image and the second image are different imaging modality types and an automated determination mechanism is used to identify the area corresponding to the location of the ROI; and causing the auto-focus tool to automatically: focus a first field of view on the ROI in the first image; focus a second field of view on the area corresponding to the location of the ROI in the second image.

In a first alternative aspect, the method comprises receiving a selection of a bounding box in a mammography image of a plurality of images, the bounding box identifying an ROI; identifying, using an auto-focus tool, a location of the ROI within the mammography image; identifying, using the auto-focus tool, an area corresponding to the location of the ROI in at least a tomography slice image of the plurality of images and an MRI image of the plurality of images; and causing the auto-focus tool to automatically: magnify the ROI in a field of view of the tomography slice image; and pan to at least one of: a breast comprising the ROI or an image plane identifying the ROI in a field of view of the MRI image.

In a second alternative aspect, the method comprises receiving a selection of a bounding box in a mammography image of a plurality of images, the bounding box identifying an ROI; identifying, using an auto-focus tool, a location of the ROI within the mammography image; identifying, using the auto-focus tool, an area corresponding to the location of the ROI in at least a tomography slice image of the plurality of images, an ultrasound image of the plurality of images, and an MM image of the plurality of images; and causing the auto-focus tool to automatically: magnify the ROI in a field of view of the tomography slice image; pan to a breast comprising the ROI in a field of view of the ultrasound image; and pan to at least one of: a breast comprising the ROI or an image plane identifying the ROI in a field of view of the MRI image.

In an example, the system is an electronic image review system for reviewing medical images within a healthcare environment. In another example, focusing the first field of view on the ROI in the first image comprises centering the ROI within the first field of view and scaling the ROI to increase or decrease a size of the ROI within the first field of view. In another example, the imaging modality types include at least two of: mammography, MM, or ultrasound.

In another example, the first image is generated during a current patient visit for a patient and the second image was generated during a previous patient visit for the patient. In another example, the plurality of images is arranged for viewing based on an image viewing layout specified by a user, the image viewing layout enabling the plurality of images to be concurrently presented to a user.

In another example, receiving the selection of the ROI comprises: receiving a selection of a point in the first image; and defining an area surrounding the point as the ROI, wherein in response to receiving the selection of the point in the first image, a bounding box comprising at least a portion of the ROI is automatically applied to the image such that at least a first object in the first image is delineated from at least a second object in the first image. In another example, receiving the selection of the ROI comprises: receiving a selection of a plurality of points in the first image; determining a centroid of the plurality of points; and defining an area surrounding the centroid as the ROI. In another example, the automated determination mechanism is at least one of: a rule set, a mapping algorithm, or an image or object classifier. In another example, a process for identifying the location of the ROI within the first image is based on the imaging modality type of the first image and the process includes the use of at least one of: image view information, spatial coordinate information, image header information, or image orientation data.

In another example, when the first image and a third image of a plurality of images are a same imaging modality type, a mapping function is used to map first ROI identification information of the first image to second ROI identification information of the third image such that the first ROI identification information and the second ROI identification information are a same type. In another example, a mapping function is used to convert first ROI identification information of the first image to second ROI identification information of the second image such that the first ROI identification information and the second ROI identification information are a different type. In another example, focusing the first field of view on the ROI in the first image comprises orienting the first image such that the ROI is at least one of horizontally or vertically centered in a viewport comprising the first image. In another example, wherein focusing the second field of view on the area corresponding to the location of the ROI in the second image comprises applying a scaling factor to the area corresponding to the location of the ROI.

In another aspect, examples provided in the present disclosure relate to a method comprising: receiving, at an image review device, a selection of a region of interest (ROI) in a first image of a plurality of images; identifying, using the auto-focus tool, a location of the ROI within the first image; identifying, using the auto-focus tool, an area corresponding to the location of the ROI in at least a second image of the plurality of images, wherein the first image and the second image are different imaging modality types and an automated determination mechanism is used to identify the area corresponding to the location of the ROI; and causing the auto-focus tool to automatically: focus a first field of view on the ROI in the first image; and focus a second field of view on the area corresponding to the location of the ROI in the second image. In an example, the plurality of images comprises at least a mammography image, an MRI image, and an ultrasound image.

In yet another aspect, examples provided in the present disclosure relate to a computing device comprising: a processor; and an image auto-focus tool configured to: receive a selection of a region of interest (ROI) in a first image of a plurality of images; identify a location of the ROI within the first image; identify an area corresponding to the location of the ROI in at least a second image of the plurality of images, wherein the first image and the second image are different imaging modality types and an automated determination mechanism is used to identify the area corresponding to the location of the ROI; focus a first field of view on the ROI in the first image; and focus a second field of view on the area corresponding to the location of the ROI in the second image, wherein focusing the second field of view comprises at least one of scaling the second image or panning the second image.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

Figure 1:
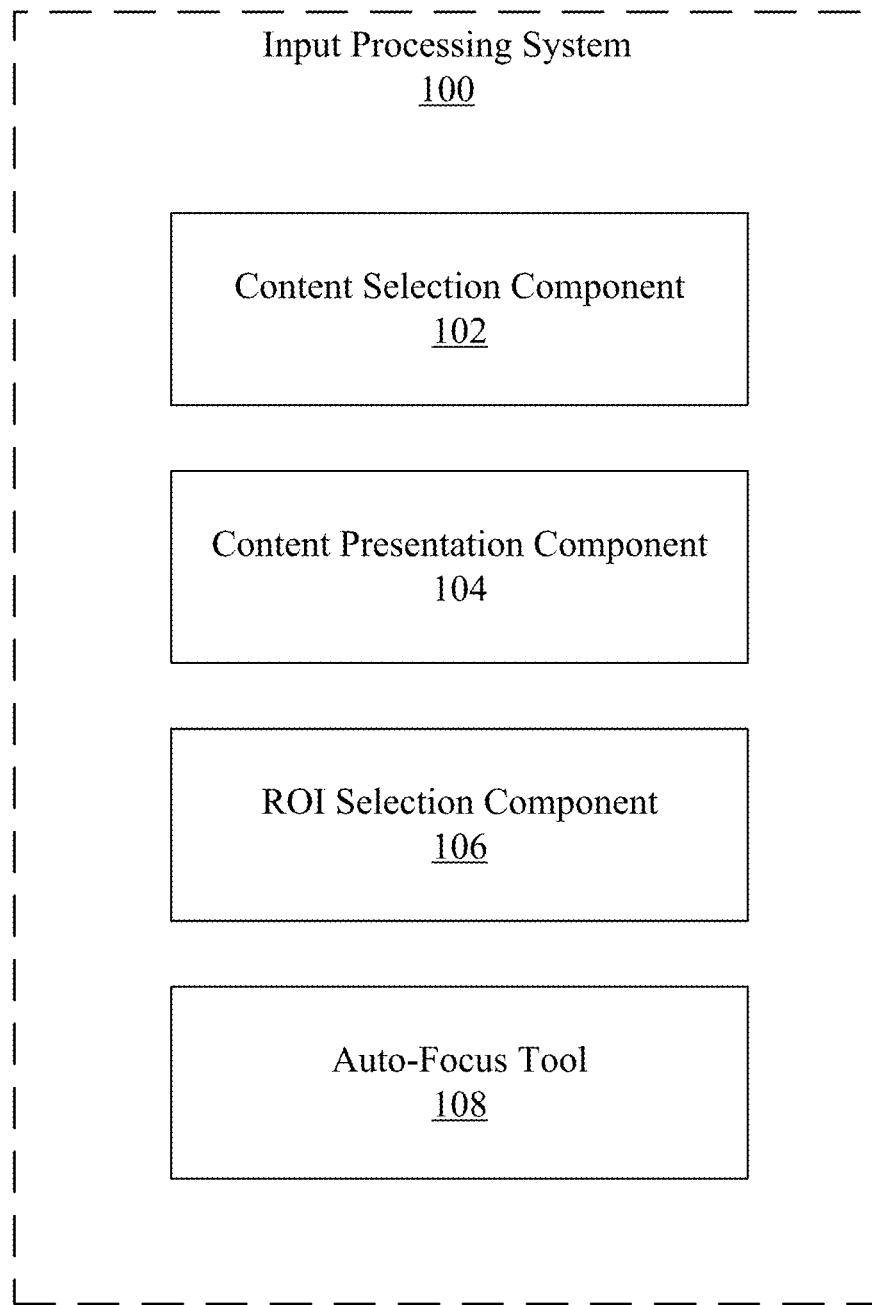
FIG. 1 illustrates an example input processing system for an auto-focus tool for multimodality image review, as described herein.

Medical imaging has become a widely used tool for identifying and diagnosing ROIs and abnormalities, such as cancers or other conditions, within the human body. Medical imaging processes such as mammography and tomosynthesis are particularly useful tools for imaging breasts to screen for, or diagnose, cancer or other lesions within the breasts. Tomosynthesis systems are mammography systems that allow high resolution breast imaging based on limited angle tomosynthesis. Tomosynthesis, generally, produces a plurality of X-ray images, each of discrete layers or slices of the breast, through the entire thickness thereof. In contrast to conventional two-dimensional (2D) mammography systems, a tomosynthesis system acquires a series of X-ray projection images, each projection image obtained at a different angular displacement as the X-ray source moves along a path, such as a circular arc, over the breast. In contrast to conventional computed tomography (CT), tomosynthesis is typically based on projection images obtained at limited angular displacements of the X-ray source around the breast. Tomosynthesis reduces or eliminates the problems caused by tissue overlap and structure noise present in 2D mammography imaging.

In recent times, healthcare professionals have expressed a clinical need for an automated solution to correlate ROIs in medical images acquired from various imaging modalities, such as mammography, synthesized mammography, tomosynthesis, wide angle tomosynthesis, ultrasound, computed tomography (CT), and magnetic resonance imaging (MM). Proposed solutions have typically involved the use of various ML approaches, which require a vast amount of diverse training data that is generally not readily available for clinical use. Acquiring and using the training data to train an ML model or algorithm, thus, requires a substantial resource investment. This resource investment is further exacerbated by the substantial computing resources (e.g., central processing unit (CPU), memory, and file storage resources) demand required to operate the trained ML model or algorithm. In many cases, the analysis performed by a trained ML model or algorithm is slow (due to the computing resource demand) and the results of the trained ML model or algorithm are inaccurate or imprecise.

For the above reasons, the ROI correlation is still primarily performed manually by healthcare professionals. For example, healthcare professionals use image manipulation tools, such as pan and zoom tools, to focus on an ROI or narrow a field of view in an image. However, the use of such image manipulation tools often results in excessive mouse clicks and movements that impede image review workflow and cause healthcare professionals to fatigue. For instance, when using such image manipulation tools, a user must select multiple tools to accomplish a specific task. Each selected tool must be applied to each image or viewport in a set of medical images to enable the user to manually pan and/or zoom the image/viewport. Each instance of manual panning/zooming may result in multiple mouse clicks and movements while the user attempts to achieve an optimal or acceptable view of the image/viewport. Moreover, in some cases, the image manipulation tools are specific to a particular imaging modality or imaging system (e.g., the image manipulation tools are not multimodal). For instance, a first set of image manipulation tools of a first image review system may be used to view mammography images and a second set of image manipulation tools of a second image review system may be used to view MRI images. To compare the mammography images to the MM images, a healthcare professional may display the mammography and MRI images on separate display screens and manually orient the respective images on each display screen using the respective image manipulation tools. The use of different sets of image manipulation tools is cumbersome, complicated, and requires healthcare professionals to be proficient using multiple sets of image manipulation tools.

To address such issues with traditional methods for ROI correlation, the present disclosure describes systems and methods for an auto-focus tool for multimodality image review. In aspects, an image review system may provide for the display of a set of medical images representing one or more imaging modalities, such as mammography, tomosynthesis, MRI, and ultrasound, among others. As a specific example, the set of medical images may include a current mammography image of a patient's breast (collected during a current patient visit) and one or more prior mammography images of the patient's breast (collected during one or more previous patient visits). Displaying the set of medical images may include the use of one or more hanging protocols. A hanging protocol, as used herein, may describe what images to display (e.g., image attributes and conditions, including modality, anatomy, laterality, procedure, and reason) and how to display the images (e.g., viewport height or width; image zoom, pan, or rotation, image order, tiling). The hanging protocols may enable the simultaneous or concurrent display of multiple images within respective viewports of a display screen. A viewport, as used herein, may refer to a frame, a sub window, or a similar viewing area within a display area of a device. As used herein, a mammography image may refer to an image acquired on a conventional two-dimensional (2D) mammography system or a synthesized 2D image that is created from combining information from a tomosynthesis data set. For ease of reading, both can be referred to as a mammogram or a mammography image.

The system may also provide an auto-focus tool that may be used during the review of the set of medical images. The auto-focus tool may provide for automatically orienting (e.g., panning, zooming, centering, aligning) images in the set of medical images in accordance with a selected portion of an image in the set of medical images. Upon activation of the auto-focus tool, the system may enable a user, such as a healthcare professional (e.g., a radiologist, a surgeon or other physician, a technician, a practitioner, or someone acting at the behest thereof) to select an ROI in a displayed image. Alternatively, the selection of the ROI in a displayed image may cause the auto-focus tool to be activated or be part of the process for activating the auto-focus tool. The auto-focus tool may identify the location of the selected ROI within the image based on image attributes, such as view position information (e.g., bilateral craniocaudal (CC) view, mediolateral oblique (MLO) view, true lateral view), laterality (e.g., left, right), image coordinates and direction information (e.g., image position and image orientation with respect to the patient), and other information embedded in the DICOM header (e.g., pixel spacing, slice thickness, slice location) or information burned in the pixel data of the image. Additionally, information within an image, such as segmentation bounding box information (e.g., object-background differentiation data, skin-tissue demarcation data, and similar object classification data) may be used for identification.

The auto-focus tool may use the identified ROI location to associate a corresponding area or ROI in each of the other images in the set of medical images. The areas or ROIs in the other images may be identified using the image characteristics described above. As one example, a bounding box area of an identified ROI in a first mammography image may be used to identify the same bounding box area in a second mammography image of the same view position. As another example, a bounding box area of an identified ROI in a first mammography image may be used to set the viewing plane, set the display field of view, or set the size of an MRI image; the location may correspond to the selected ROI in a first mammography image and may be oriented and scaled according to the position, size, and location of the selected ROI.

After identifying the corresponding ROIs in the other images, the auto-focus tool may orient the set of medical images such that the identified ROI is prominently displayed in the set of medical images. For example, in each image in the set of medical images, the auto-focus tool may pan to, zoom in on, and/or center (within the respective viewport for the image) an area of the image corresponding to the identified ROI. As such, the auto-focus tool serves as a single tool that replaces (or minimizes) the need for several other tools (e.g., pan tool, zoom tool, centering/alignment tools, scroll tool, orientation tool) and enables healthcare professionals to quickly and efficiently focus on, for example, a patient's breast or a region within the patient's breast. These capabilities of the auto-focus tool improve image review workflow and decrease the fatigue of healthcare professionals (due to decreased mouse clicks and movements) during image review.

Accordingly, the present disclosure provides a plurality of technical benefits including but not limited to: automating ROI correlation in images having the same and/or different imaging modalities, consolidating multiple image manipulation tools into a single tool, enabling multimodal image review in a single system, improving image review workflow, and decreasing healthcare professional fatigue during image review, among others.

FIG. 1 illustrates an example input processing system for an auto-focus tool for multimodality image review. Although examples in FIG. 1 and subsequent figures will be discussed in the context of image content, the examples are equally applicable to other types of content, such as video content and text content. In some examples, one or more data and components described in FIG. 1 (or the functionality thereof) may be distributed across multiple devices. In other examples, a single device may comprise the data and components described in FIG. 1.

In FIG. 1, input processing system 100 comprises content selection component 102, content presentation component 104, ROI selection component 106, and auto-focus tool 108. One of skill in the art will appreciate that the scale of input processing system 100 may vary and may include additional or fewer components than those described in FIG. 1. As one example, input processing system 100 may comprise one or more additional content selection components 102, each of which may correspond to a different imaging system or imaging modality. As another example, the functionality of ROI selection component 106 may be integrated into auto-focus tool 108.

In examples, input processing system 100 may represent a content review and manipulation system, such as a medical image review system. Input processing system 100 may be implemented in a secure computing environment comprising sensitive or private information, such as a healthcare facility (e.g., a hospital, an imaging and radiology center, an urgent care facility, a medical clinic or medical offices, an outpatient surgical facility, or a physical rehabilitation center). Alternatively, one or more components of input processing system 100 may be implemented in a computing environment external to the secure computing environment.

Content selection component 102 may be configured to enable content to be selected from one or more data sources. For example, content selection component 102 may have access to multiple data stores comprising image data of a medical imaging technology, such as picture archiving and communication system (PACS) or radiology information system (RIS). A user, such as a healthcare professional, may use content selection component 102 to select images (and associated image content) of one or more imaging modalities, such as mammography, ultrasound, and MRI. The images may be selected using a user interface provided by content selection component 102. The user interface may enable the user to select images by various criterion, such as patient name/identifier, imaging modality type, image creation/modification date, image collection/generation location, etc.

Content presentation component 104 may be configured to present selected content to a user. For example, content presentation component 104 may enable a user to select or define a content presentation style or layout, such as a hanging protocol, using the user interface (or a separate user interface). Alternatively, a default content presentation style or layout may be applied to the content presentation style or layout. Based on the selected or applied content presentation style or layout, content presentation component 104 may arrange the selected content into one or more viewports. For instance, a patient's current mammography image may be arranged into a leftmost viewport, the patient's mammography image from a patient visit one year ago may be arranged into a center viewport, and the patient's mammography image from a patient visit two years ago may be arranged into a rightmost viewport. In examples, the images in each viewport may be manipulated independently from the other presented viewports. That is, a user may manipulate (e.g., orient, pan, scroll, apply window level, annotate, remove, or otherwise modify) an image in a first presented viewport without affecting images in other presented viewports.

ROI selection component 106 may be configured to enable a user to select an area or point in the presented content. For example, the user interface may comprise one or more area selection mechanisms for identifying an ROI within an image presented in a viewport. In some aspects, an area selection mechanism may be automated to automatically identify an ROI within an image. For instance, ROI selection component 106 may implement an image recognition algorithm or model. The algorithm/model may enable processing an image (and other content) to identify and analyze objects and attributes of the image. Examples of the algorithm/model may include convolution neural networks (CNN), bag-of-words, logistic regression, support vector machines (SVM), and k-nearest-neighbor (KNN). In examples, the algorithm/model may automatically overlay a segmentation bounding box (or a similar area selection utility) on an image. The bounding box may identify and/or delineate one or more objects in the image. As a specific example, in a mammography image, the bounding box may encompass a patient's breast such that the breast is delineated from the background of the image or from other content (e.g., annotations or embedded data) within the image. In other aspects, an area selection mechanism may be used by a user to manually select an ROI within an image. For instance, ROI selection component 106 may provide an input tool, such as a cursor or pointer object, an enclosure tool (e.g., elliptical ROI, rectangular ROI, freehand ROI), or a highlighting tool. A user may use the input tool to specify a point or region of the image.

Auto-focus tool 108 may be configured to enable multimodality image review of the presented content. For example, the user interface may comprise auto-focus tool 108 or may enable a means for activating auto-focus tool 108 (e.g., a command button, a menu item, a keyboard sequence, a voice command, an eye-gaze command). A user may activate auto-focus tool 108 after selection of an ROI in presented content. Alternatively, the user may activate auto-focus tool 108 prior to selection of the ROI. For instance, activation of auto-focus tool 108 may cause the activation of ROI selection component 106.

Upon selection of auto-focus tool 108 and/or the ROI, auto-focus tool 108 may identify the location of the ROI within the content from which the ROI was selected ("source content"). The process for identifying the location of the ROI may differ based on the type of imaging modality for the source content. As one example, for a mammography image, auto-focus tool 108 may identify the location of an ROI based on image view information, such as laterality (e.g., right breast or left breast) and view position (e.g., MLO, CC). For instance, an area of the mammography image corresponding to the upper region of a MLO view of a right breast may be selected as the ROI.

As another example, for an MM image, auto-focus tool 108 may identify the location of an ROI based on DICOM header information, which may include image position and slice information, for the MRI image. For instance, the header information for the MM image may contain image orientation and image position information that can be used to determine spatial coordinates of objects, boundaries, and/or landmarks within the image using the Reference Coordinate System (RCS). Using the information embedded in the header spatial coordinates corresponding to the ROI may be identified. In some instances, the spatial coordinates for the ROI may be converted to or defined in terms of coordinates relative to the patient, such as right/left, anterior/posterior, and feet/head positions.

As yet another example, for an ultrasound image, auto-focus tool 108 may identify the location of an ROI based on DICOM header information and/or pixel data embedded in the image. For instance, the header information for the ultrasound image may indicate image laterality (e.g., right or left) and/or the header information of objects associated with the ultrasound image, such as Grayscale Softcopy Presentation State (GSPS) objects, may contain information embedded in the annotation that captures the location. Alternatively, the annotations may be embedded in the pixel data of the ultrasound image and describes the location of the ROI. In at least one example, auto-focus tool 108 may also use movement data for the ultrasound device to identify the location of an ROI. For instance, position and movement data for an ultrasound transducer or probe may be recorded during the ultrasound imaging.

Auto-focus tool 108 may use the identified location of the ROI in the source content to identify a corresponding area in the other presented content. The method for identifying the corresponding areas may differ based on the type of imaging modality of the other presented content. In some aspects, when the source content and the other presented content is the same imaging modality type, auto-focus tool 108 may map the image view information, spatial coordinate information, header information, and/or pixel data of the ROI to the corresponding area in the other presented content. As one example, in a first mammography image (source content), an identified ROI may be in the upper inner quadrant of a CC view of a patient's right breast. Accordingly, in a second mammography image (other presented content), auto-focus tool 108 may identify the upper inner quadrant of a CC view of the patient's right breast. As another example, in a first MRI image for a patient (source content), the slice information (e.g., middle slice) and spatial coordinate information of an identified ROI may be mapped to the same image slice and coordinates in a second MRI image for the patient. As yet another example, in a first ultrasound image for a patient (source content), the laterality information associated with an identified ROI may be used to identify a second ultrasound image of the same laterality.

In other aspects, when the source content and the other presented content is a different imaging modality type, auto-focus tool 108 may convert the header information of the image, such as image view information or spatial information, or information contained in objects associated with the image or embedded in the pixel data into information corresponding to the other presented content type. As one example, auto-focus tool 108 may convert the image view position or laterality information associated with an ROI in a mammography image (source content) into a slice location or set of spatial coordinates approximating the corresponding location of the ROI in an MM image (other presented content). For instance, a mammography image of the CC view position and right laterality may correspond to the middle portion of the right breast from a bilateral breast MM image. As another example, the location of the ROI in the mammography image or information contained in associated objects (e.g., GSPS, CAD SR) may be mapped to set of MRI coordinates corresponding to the location of the ROI. Determining the spatial coordinates of the ROI or determining the laterality, quadrant, or region of the breast where the ROI resides, may include the use of one or more determination mechanisms, such as a rule set, decision logic, an ML component (e.g., algorithm/model), a mapping algorithm, etc.

As another example, auto-focus tool 108 may convert the image view information of an ROI in a mammography image (source content) into view laterality information identifying an ultrasound image (other presented content). As neither the mammography image nor the ultrasound image may comprise spatial coordinate information, the laterality information in the image view information may be used to identify a corresponding ultrasound image (e.g., an ultrasound image of similar laterality). Identifying the corresponding ultrasound image may include the use of at least one of the determination mechanisms.

As yet another example, auto-focus tool 108 may convert the spatial coordinates of an ROI in an MRI image (source content) into laterality information identifying an ultrasound image (other presented content). For instance, the sagittal midline of a patient's body may represent a patient's origin according to the Reference Coordinate System such that positive values in the X direction, or values to the left of the midline, indicate areas in or around the patient's left breast and negative values in the X direction, or values to the right of the midline, indicate areas in or around the patient's right breast. Accordingly, a determination mechanism, such as a coordinate mapping algorithm, may be used to map/convert the spatial coordinates into a laterality determination.

After identifying the corresponding area in each of the other presented content, auto-focus tool 108 may focus the field of view of each viewport such that the identified ROI and the corresponding areas are prominently displayed. For example, in the viewport comprising the source content, focus tool 108 may orient the identified ROI such that ROI is horizontally and/or vertically centered in the viewport. The orienting may occur automatically and in real-time in response to the selection of the auto-focus tool 108 and/or the ROI. Additionally, focus tool 108 may magnify the ROI to further focus the attention of a user on a particular region of the breast (e.g., upper inner quadrant, lower outer quadrant). In the viewports of the other presented content, focus tool 108 may similarly orient the areas corresponding to the ROI in the source content. As one example, an MRI image in a viewport may be oriented such that the center slice from the right side or left side of the patient (right breast or left breast) is displayed regardless of whether the ROI in the source content is located more internal (medial) or more external (lateral) for one breast. In such an example, the center slice may serve as a general or starting focus area for the user. As another example, an MM image in a viewport may have its focus set on the upper region of the breast based on the location of the ROI in the source content.

Having described a system and process flow that may employ the techniques disclosed herein, the present disclosure will now describe one or more methods that may be performed by various aspects of the present disclosure. In aspects, method 200 may be executed by a system, such as system 100 of FIG. 1. However, method 200 is not limited to such examples. In other aspects, method 200 may be performed by a single device comprising multiple computing environments. In at least one aspect, method 200 may be executed by one or more components of a distributed network, such as a web service/distributed network service (e.g., cloud service).

Figure 2:
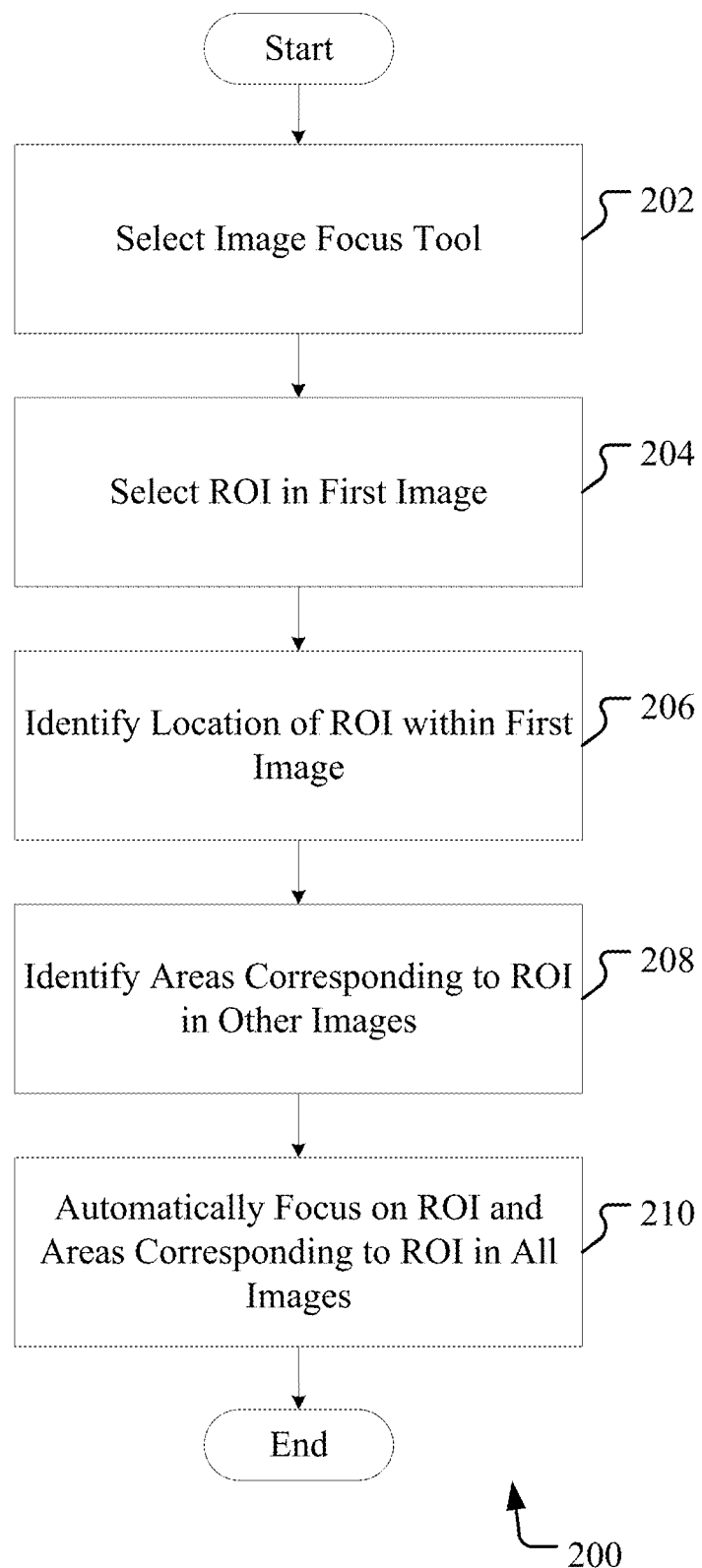
FIG. 2 illustrates an example method for utilizing an auto-focus tool for multimodality image review, as described herein

FIG. 2 illustrates an example method for utilizing an auto-focus tool for multimodality image review. Example method 200 may be executed by a user, such as a healthcare provider, in a computing environment comprising sensitive or private information associated with, for example, a healthcare facility, healthcare patients, and/or healthcare personnel. The computing environment may comprise an electronic image review system, such as input processing system 100. The image review system may enable the user to retrieve images from various data sources, such as data store(s) 106. The retrieved images may represent images of various imaging modalities, such as mammography, ultrasound, MRI, etc. The user may arrange the retrieved images for viewing and manipulating based on an image viewing layout, such as a hanging protocol. The image viewing layout may provide for the simultaneous display of images of varying (or similar) imaging modalities. As a specific example, the image viewing layout may comprise four viewports (each comprising an image) arranged in a left-to-right configuration.

Example method 200 begins at operation 202, where an image focus tool is selected. In aspects, the image review system may comprise or provide access to an image focus tool, such as auto-focus tool 108. For example, the image review system may provide a user interface component (e.g., graphical user interface (GUI), command line, microphone, haptic mechanism, camera) for selecting and/or activating the image focus tool. A user using the image review system to view one or more images may use the user interface component to select and activate the image focus tool. Alternatively, the user may select and activate the image focus tool prior to accessing, retrieving, or viewing the images.

At operation 204, an ROI in a first image may be selected. In aspects, a user may use an input tool (e.g., cursor, stylus, enclosure tool, highlighting tool, voice-based tool, eye-gaze tool) provided by the image focus tool or the image review system to select one or more points or portions of an image. For instance, the user may select a point in a first image of image viewing layout comprising four images. The selected points or portions may define a ROI. As one example, when a single point in an image is selected, an area surrounding the single point may be defined as the ROI. As another example, when multiple points in an image are selected, the image focus tool may determine a centroid (or approximate center point) of the multiple points. An area surrounding the centroid may be defined as the ROI. The amount and/or shape (e.g., ellipse, rectangle, freeform) of the area used to define the ROI may be determined automatically by the image focus tool or defined manually by the user. For instance, the image focus tool may automatically overlay the image with a bounding box that encompasses the selected/determined point. The bounding box may delineate one or more objects in the image from other objects or the background of the image.

At operation 206, the location of the ROI within the first image may be identified. The process for identifying the location of the ROI may include the use of one or more determination mechanisms (e.g., a rule set, decision logic, an ML component, a mapping algorithm, image or object classifier) and may differ based on the imaging modality type of the first image. As one example, the image focus tool may use a set of data extraction rules to identify ROI in a mammography image using image view information of the mammography image, such as laterality (e.g., right or left) and view position (e.g., MLO, CC). For instance, the data extraction rules may label or otherwise designate the ROI as "CC View, Right Breast" based on the information in a Digital Imaging and Communication in Medicine (DICOM) header of the mammography image. Alternatively, the ROI may be further labeled/designated using additional area information in the image, such as "Right Breast, Upper Outer Quadrant."

As another example, the image focus tool may use a spatial mapping function to identify ROI in an MRI image using information available in the DICOM header of an MRI image and/or associated objects, such as Image Position (Patient), Image Orientation (Patient), Pixel Spacing, Slice Thickness, and Slice Location. The spatial mapping function may define the ROI using a 3D reference coordinate system (e.g., x, y, and z coordinates) in which the boundary of the ROI is defined by multiple sets of coordinate values or defined in terms of right/left, anterior/posterior, and feet/head coordinate values that are relative to the patient (e.g., L:52.2, A:5.5, H:10.6). Alternatively, the ROI may be defined by a single set of coordinate values (e.g., voxel (50, 100, 55)) representing the center (or centroid) of the ROI.

As another example, the image focus tool may use a text recognition algorithm to identify ROI in an ultrasound image using image header information, pixel data, orientation data, and/or imaging device data, such as laterality information (e.g., right or left), embedded image information (e.g., annotations and notes), and 2D/3D transducer/probe movement data. For instance, the text recognition algorithm may generally label or otherwise designate the ROI as "Right Breast" based on text-based laterality information extracted from the DICOM header of the ultrasound image. Alternatively, the ROI may be labeled/designated based on embedded annotations (e.g., handwritten notes, burned-in text) and/or an orientation map in the image data of the ultrasound image.

At operation 208, areas corresponding to the ROI may be identified in other images. In aspects, the image focus tool may use the identified location of the ROI within the first image to identify corresponding areas in the other images presented in the image viewing layout. The process for identifying the corresponding areas in the other images may include the use of one or more of the determination mechanisms described above (and/or additional determination mechanisms and may differ based on the imaging modality type of the other images. As one example, when the imaging modality type of the first image matches the imaging modality type of a second image, a mapping function may be used to map the ROI identification information of the first image (e.g., image view information, spatial coordinate information, header information) to the same (or similar) ROI identification information of the second image. For instance, the ROI label/designation "Right Breast, Upper Outer Quadrant" for a first mammography image may be used by the mapping function to map the same laterality (e.g., right breast) and region (e.g., Upper Outer Quadrant) in a second mammography image based on the image view information for the second mammography image.

As another example, when the imaging modality type of the first image does not match the imaging modality type of a second image, a mapping function may be used to map the ROI identification information of the first image (e.g., image view information, spatial coordinate information, header information) to different, but corresponding ROI identification information of the second image. For instance, the ROI label/designation "Right Breast, Axillary Region" for a mammography image may be converted to a set of MRI spatial coordinates. The set of MRI spatial coordinates may be predefined for one or more areas in each type of mammography image. As a specific example, spatial coordinates may be predefined for the various quadrants of the breast (e.g., Upper Outer, Upper Inner, Lower Outer, Lower Inner), regions (e.g., Central, Retroareolar, Axillary), and/or laterality (e.g., right, left) of the mammography image. Accordingly, the ROI label/designation for a mammography image may be used to select the corresponding MRI spatial coordinates in an MRI image.

At operation 210, the images may be automatically focused on the ROI and corresponding areas. In aspects, the image focus tool may focus the field of view of each image in the image viewing layout such that the ROI and corresponding areas are prominently displayed. For example, after (or prior to) identifying the areas corresponding to the ROI, the image focus tool may orient the identified ROI in the first image such that ROI is horizontally and/or vertically centered in the viewport comprising the first image. The image focus tool may also (simultaneously or subsequently) orient the other images such that the areas corresponding to the ROI are horizontally and/or vertically centered in their respective viewports and may also display the areas in an orientation that is different from the original image acquisition plane, for example displaying in one or more MRI images (presented content) the axial, sagittal, and/or coronal plane to provide different perspectives of the ROI. In some examples, the image focus tool may apply some degree of scaling, magnification, and/or filtering to one or more of the images. For instance, the image focus tool may apply a 2× scaling factor to a second image and a 4× scaling factor to a third image. As should be appreciated, the automatic orientation and scaling operations of the image focus tool reduces the amount of image manipulation tools, input device clicks (and other type of selections), and input device movements required to review images. The image focus tool also enables users to review images of differing imaging modality types using the same system and image review tool. Accordingly, the image focus tool improves the image review workflow, reduces the fatigue experienced by healthcare professional fatigue during image review, and may reduce the need to learn and operate multiple image review systems and image review tools.

Figure 3A:
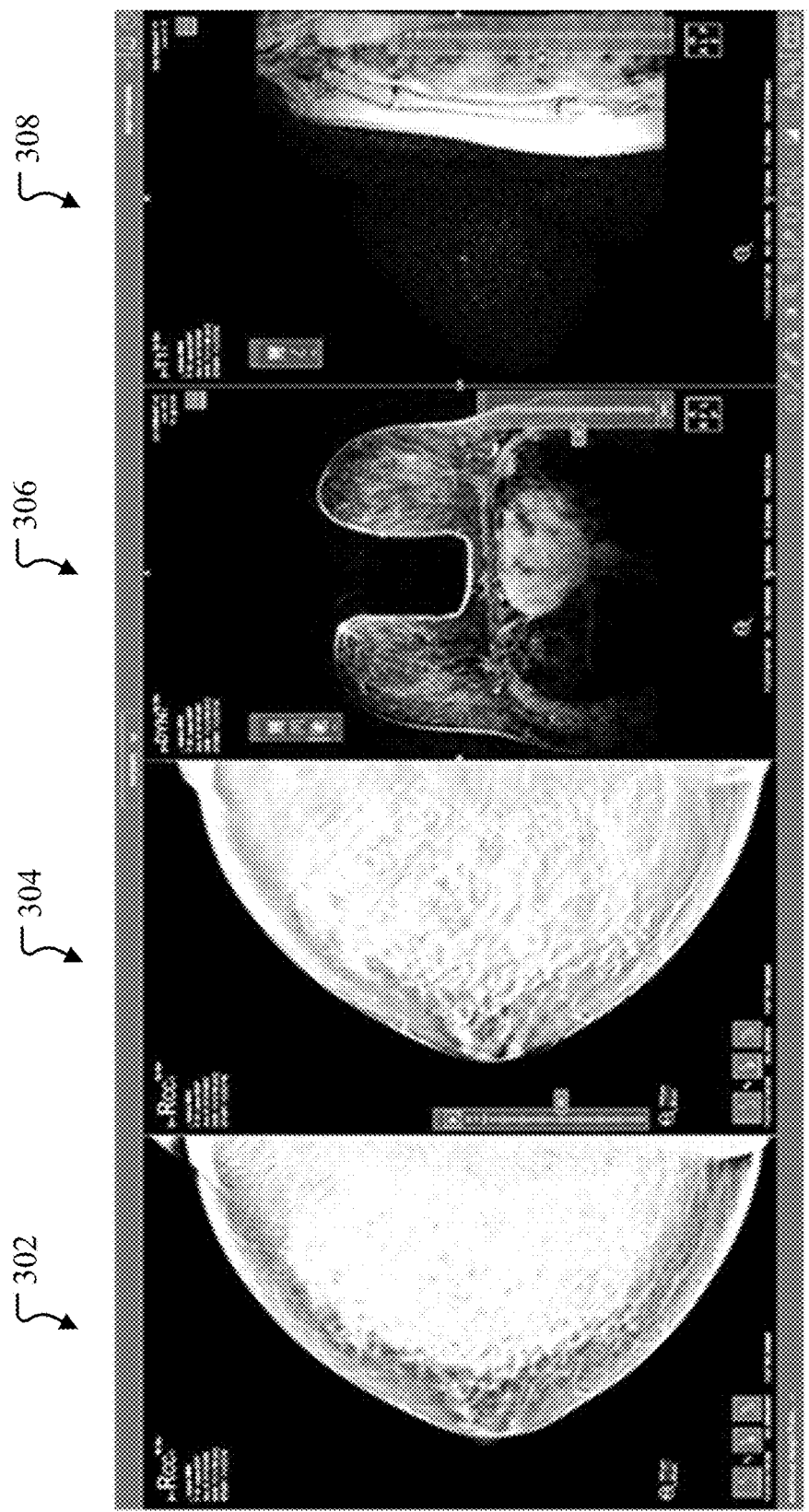
FIGS. 3A and 3B depict a set of multimodality images for illustrating the functionality of the auto-focus tool, as described herein.
Figure 3B:
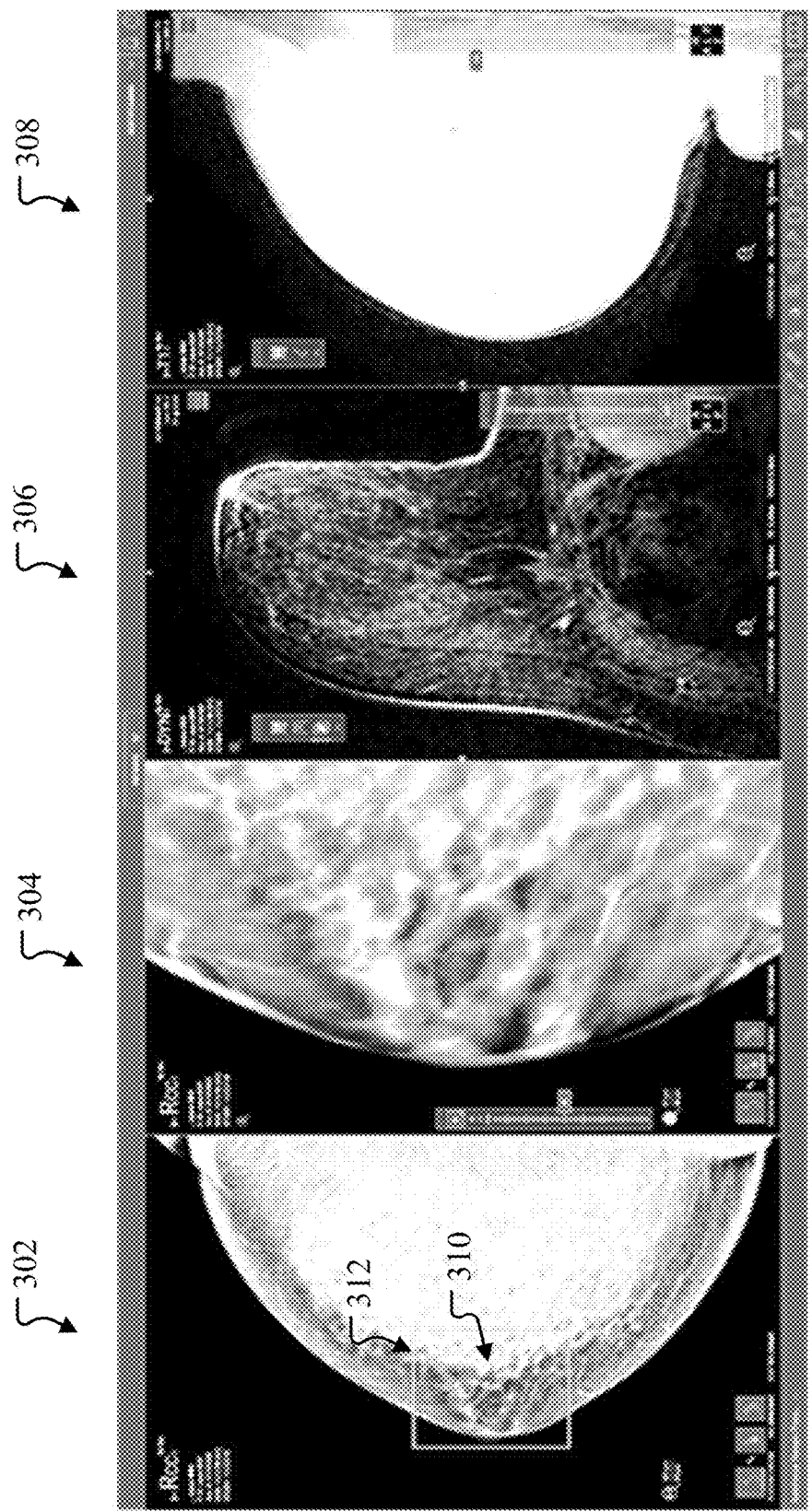

FIGS. 3A and 3B depict a set of multimodality images for illustrating the functionality of the auto-focus tool described herein. The set of multimodality images depict images of a patient's breast. FIG. 3A comprises images 302, 304, 306, and 308. Image 302 is a full field digital mammography (FFDM) image of a right breast. Image 304 is a tomosynthesis reconstruction mammography image of the same laterality as image 302. Image 306 is a bilateral breast MRI image acquired and displayed in the axial plane. Image 308 is a bilateral breast MRI image displayed in the sagittal plane at a location that centers the patient. In at least one example, each of images 302, 304, 306, and 308 may represent a different image and one or more of images 302, 304, 306, and 308 may be collected/generated at different times. For instance, image 302 may represent a control image collected during a current (or recent) patient visit and images 304, 306, and 308 may represent images collected during one or more previous patient visits. In response to selecting an ROI of image 302, images 304, 306, and 308 may be manipulated to focus on (e.g., pan, zoom, flip, rotate, center, reconstructed) the ROI in the respective images while image 302 remains unchanged. In another example, each image may represent the same image, but rendered and presented in a different way, for example reconstructing an MRI image acquired in the axial plane to a sagittal or coronal image.

In FIG. 3B, ROI 310 has been selected in image 302. In response to the selection of ROI 310, the auto-focus tool described herein has automatically set the focus for images 302, 304, 306, and 308. For example, in image 302, the auto-focus tool has applied bounding box 312 to encompass ROI 310 while the alignment and magnification of the image 302 remains unchanged. In image 304, the auto-focus tool has magnified the image and vertically aligned the area corresponding to the ROI with the ROI in image 302. In image 306, the auto-focus tool has panned to the area corresponding to the ROI, magnified the area corresponding to the ROI, and centered the area corresponding to the ROI in the viewport comprising image 306. In image 308, the auto-focus tool has reconstructed the MRI image to the sagittal plane, scrolled to the center slice of the breast matching the laterality of the ROI, and vertically aligned the area corresponding to the ROI with the ROI in image 302.

Figure 4:
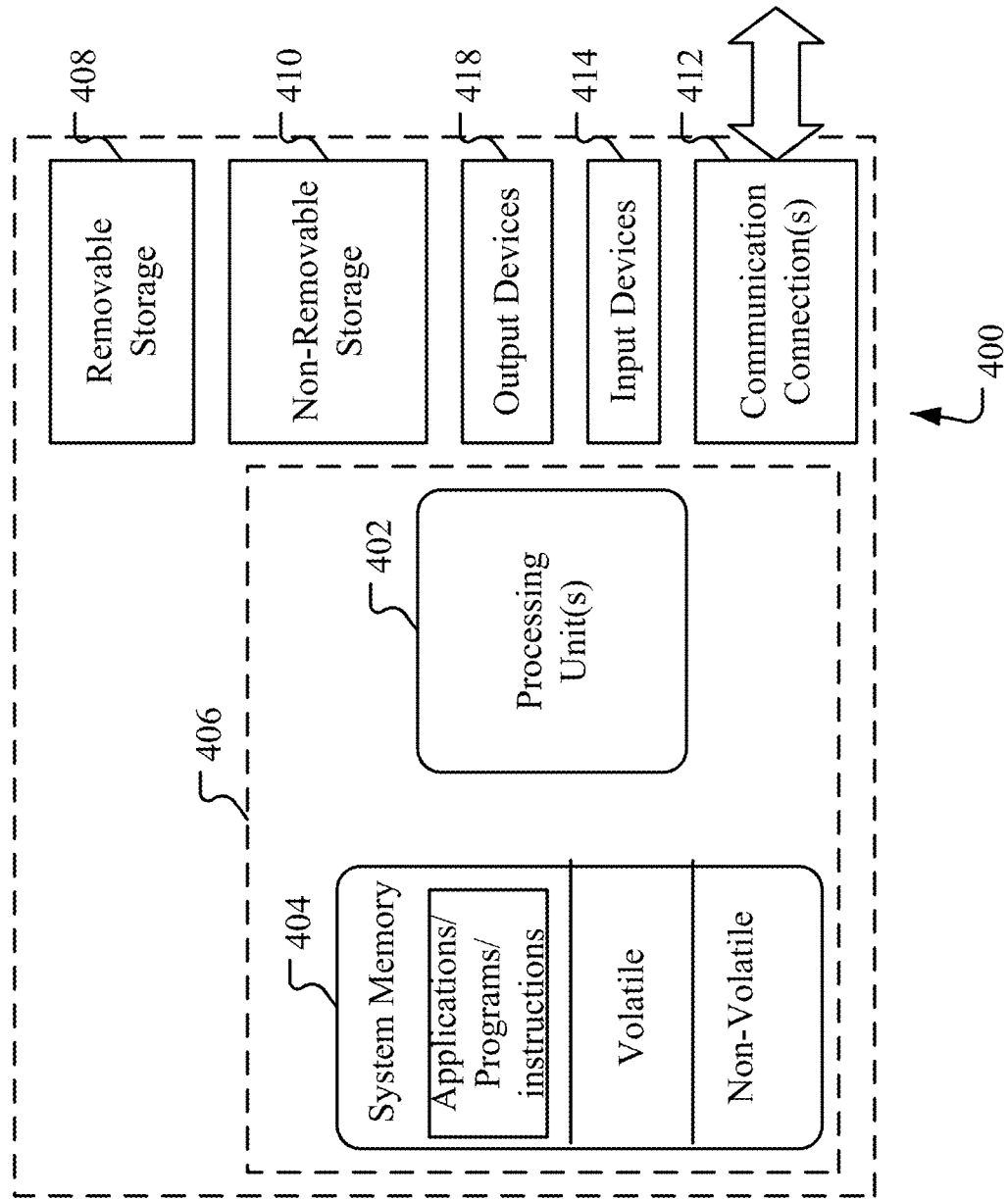
FIG. 4 illustrates one example of a suitable operating environment in which one or more of the present embodiments may be implemented.

FIG. 4 illustrates an exemplary suitable operating environment for the automating clinical workflow decision techniques described in FIG. 1. In its most basic configuration, operating environment 400 typically includes at least one processing unit 402 and memory 404. Depending on the exact configuration and type of computing device, memory 404 (storing, instructions to perform the techniques disclosed herein) may be volatile (such as RAM), nonvolatile (such as ROM, flash memory, etc.), or some combination of the two. This most basic configuration is illustrated in FIG. 4 by dashed line 406. Further, environment 400 may also include storage devices (removable, 408, and/or non-removable, 410) including, but not limited to, magnetic or optical disks or tape. Similarly, environment 400 may also have input device(s) 414 such as keyboard, mouse, pen, voice input, etc. and/or output device(s) 416 such as a display, speakers, printer, etc. Also included in the environment may be one or more communication connections 412, such as LAN, WAN, point to point, etc. In embodiments, the connections may be operable to facility point-to-point communications, connection-oriented communications, connectionless communications, etc.

Operating environment 400 typically includes at least some form of computer readable media. Computer readable media can be any available media that can be accessed by processing unit 402 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 400 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet.

Figure 5:
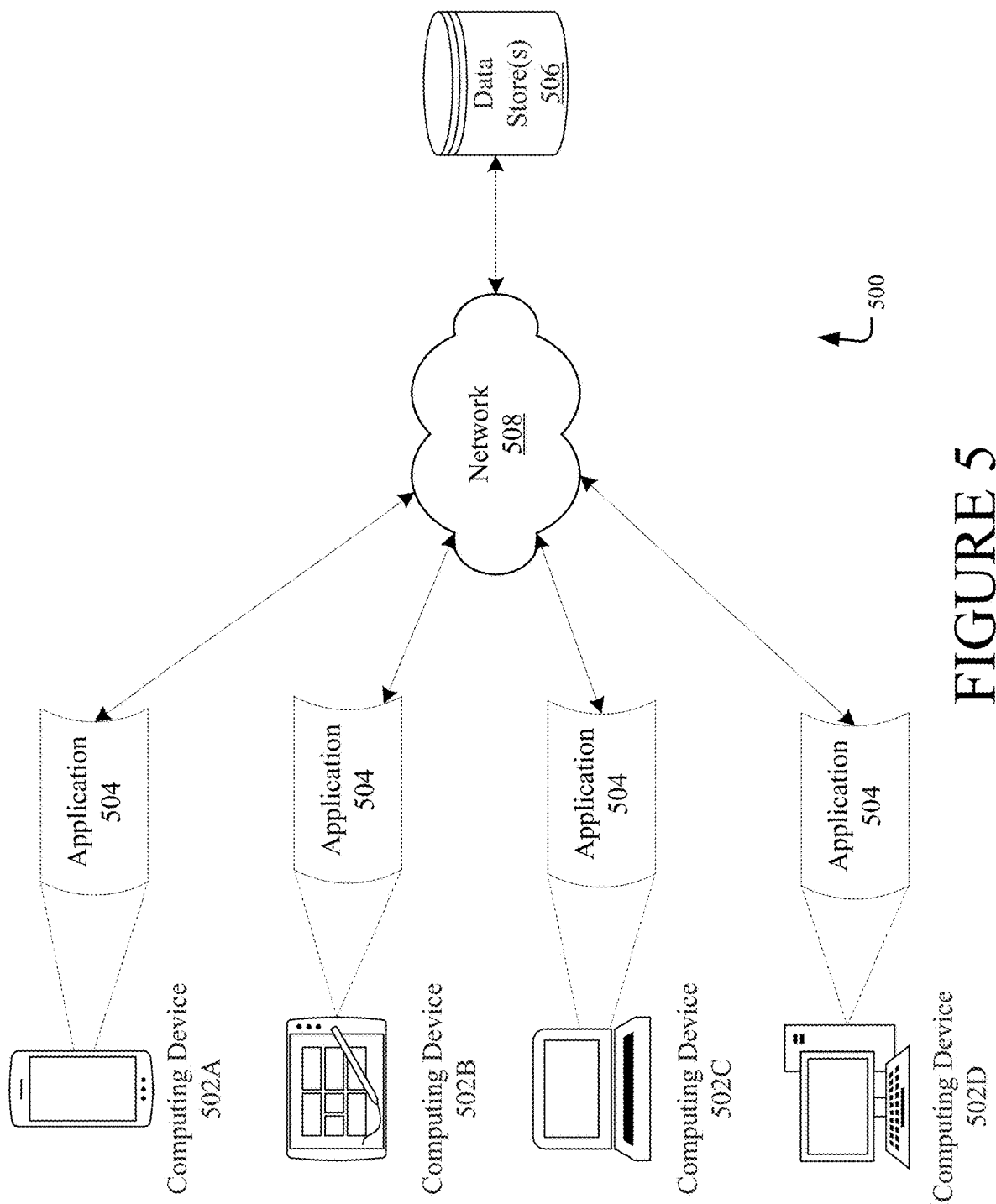
FIG. 5 illustrates an overview of an example system for an auto-focus tool for multimodality image review, as described herein.

FIG. 5 illustrates an overview of an example system for an auto-focus tool for multimodality image review. Example system 500 as presented is a combination of interdependent components that interact to form an integrated system. System 500 may comprise hardware components and/or software components implemented on and/or executed by hardware components. System 500 may provide one or more operating environments for software components to execute according to operating constraints, resources, and facilities of system 500. In some examples, the operating environment(s) and/or software components may be provided by a single processing device, as depicted in FIG. 4. In other examples, the operating environment(s) and software components may be distributed across multiple devices. For instance, input may be entered on a user device and information may be processed or accessed using other devices in a network, such as one or more network devices and/or server devices.

In aspects, system 500 may represent a computing environment comprising sensitive or private information associated with, for example, a healthcare facility, healthcare patients, and/or healthcare personnel. Although specific reference to a healthcare environment is described herein, it is contemplated that the techniques of the present disclosure may be practiced in other environments. For example, system 500 may represent a software development environment or an alternative environment that does not comprise sensitive or private medical information.

In FIG. 5, system 500 comprises computing devices 502A, 502B, 502C, and 502D (collectively "computing device(s) 502"), application 504, data store(s) 506, and network 508. One of skill in the art will appreciate that the scale of systems such as system 500 may vary and may include more or fewer components than those described in FIG. 5. As one example, the functionality and/or one or more components of application 504 may be implemented on a server device, web-based device, or in a cloud computing environment. As another example, data store(s) 508 may be integrated into computing device(s) 502.

Computing device(s) 502 may be configured to collect, manipulate, and/or display input data from one or more users or devices. For example, computing device(s) 502 may collect input data from a healthcare professional, medical equipment (e.g., imaging devices, treatment devices, monitoring devices), medical workstations, data storage locations, etc. The input data may correspond to user interaction with one or more software applications or services implemented by, or accessible to, user device(s) 502. The input data may include, for example, voice input, touch input, text-based input, gesture input, video input, and/or image input. The input data may be detected/collected using one or more sensor components of user device(s) 502. Examples of sensors include microphones, touch-based sensors, geolocation sensors, accelerometers, optical/magnetic sensors, gyroscopes, keyboards, and pointing/selection tools. Examples of user device(s) 502 may include, but are not limited to, personal computers (PCs), medical workstations, server devices, cloud-based devices, mobile devices (e.g., smartphones, tablets, laptops, personal digital assistants (PDAs)), and wearable devices (e.g., smart watches, smart eyewear, fitness trackers, smart clothing, body-mounted devices, head-mounted displays).

Computing device(s) 502 may comprise or otherwise have access to application(s) 504. Application(s) 504 may enable users to access and/or interact with one or more types of content, such as images, text, audio, images, video, and animation. As one example, application(s) 504 may represent a multimodality image processing and/or review service that enables healthcare professionals to review medical images. Although specific reference to an image processing application/service, alternative implementations are contemplated. For example, application(s) 504 may represent word processing applications, spreadsheet application, presentation applications, document-reader software, social media software/platforms, search engines, media software/platforms, multimedia player software, content design software/tools, and database applications.

Application(s) 504 may comprise or have access to one or more data stores, such as data store(s) 506. Data store(s) 506 may comprise a corpus of content of various types (e.g., images, videos, documents, files, records). For example, data store(s) 506 may include image types, such as mammography images, MRI images, ultrasound images, etc. Data store(s) 506 may be stored and accessed locally on computing device(s) 502 or stored and accessed remotely via network 508. Examples of network 508 include, but are not limited to, personal area networks (PANs), local area networks (LANs), metropolitan area networks (MANs), and wide area networks (WANs). Application(s) 504 may retrieve content from data store(s) 506. Application(s) 504 may present the content using one or more display devices or components of Computing device(s) 502. In a particular example, application(s) 504 may present the content according to a hanging protocol or a similar content display format. The hanging protocol may provide for displaying a sequence of content items, such as images, in respective viewports of the display device or component.

In some examples, application(s) 504 implements or has access to an auto-focus tool (not pictured) for reviewing presented content. The auto-focus tool may provide for automatically orienting the presented content in accordance with a user-selected area within the content. For example, a healthcare professional may select an ROI in one image of a set of presented images that includes mammography images, MRI images, and ultrasound images. The auto-focus tool may orient each of the presented images such that the identified ROI is prominently displayed in each of the images. Accordingly, the auto-focus tool may enable the healthcare professional to automatically pan to, zoom in on, set the orientation, and/or center and align (within the respective viewport for the content) an area of the content corresponding to the identified ROI in various content items.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A system comprising:
a processor; and
memory coupled to the processor, the memory comprising computer executable instructions that, when executed, perform a method comprising:
receiving a selection of a region of interest (ROI) in a first image of a plurality of images;
identifying, using an auto-focus tool, a location of the ROI within the first image based on at least one of spacing of image pixel data, thickness of a slice image, and location of the slice image;
converting, via a mapping function of the auto-focus tool, first ROI identification information of the first image to second ROI identification of at least a second image of the plurality of images, wherein the first ROI identification information and the second ROI identification information are a different type, the first ROI identification information includes image view information and the second ROI identification information includes image header information;
identifying, using the auto-focus tool, an area corresponding to the location of the ROI in at least the second image of the plurality of images, wherein the first image and the second image are different imaging modality types and an automated determination mechanism is used to identify the area corresponding to the location of the ROI; and
causing the auto-focus tool to automatically:
focus a first field of view on the ROI in the first image; and
focus a second field of view on the area corresponding to the location of the ROI in the second image.

2. The system of claim 1, wherein the system is an electronic image review system for reviewing medical images within a healthcare environment.

3. The system of claim 1, wherein focusing the first field of view on the ROI in the first image comprises centering the ROI within the first field of view and scaling the ROI to increase or decrease a size of the ROI within the first field of view.

4. The system of claim 1, wherein the imaging modality types include at least two of: mammography, MRI, or ultrasound.

5. The system of claim 1, wherein the first image is generated during a current patient visit for a patient and the second image was generated during a previous patient visit for the patient.

6. The system of claim 1, wherein the plurality of images is arranged for viewing based on an image viewing layout specified by a user, the image viewing layout enabling the plurality of images to be concurrently presented to a user.

7. The system of claim 1, wherein receiving the selection of the ROI comprises:
receiving a selection of a point in the first image; and
defining an area surrounding the point as the ROI.

8. The system of claim 7, wherein, in response to receiving the selection of the point in the first image, a bounding box comprising at least a portion of the ROI is applied to the image.

9. The system of claim 8, wherein the bounding box is automatically applied such that at least a first object in the first image is delineated from at least a second object in the first image.

10. The system of claim 1, wherein receiving the selection of the ROI comprises:
receiving a selection of a plurality of points in the first image;
determining a centroid of the plurality of points; and
defining an area surrounding the centroid as the ROI.

11. The system of claim 1, wherein the automated determination mechanism is at least one of: a rule set, a mapping algorithm, or an image or object classifier.

12. The system of claim 1, wherein a process for identifying the location of the ROI within the first image is based on the imaging modality type of the first image.

13. The system of claim 12, wherein the process for identifying the location of the ROI within the first image includes the use of at least one of: image view information, spatial coordinate information, image header information, or image orientation data.

14. The system of claim 1, wherein, when the first image and a third image of the plurality of images are a same imaging modality type, the mapping function is used to map the first ROI identification information of the first image to third ROI identification information of the third image, wherein the first ROI identification information and the third ROI identification information are a same type.

15. The system of claim 1, wherein focusing the first field of view on the ROI in the first image comprises orienting the first image such that the ROI is at least one of horizontally or vertically centered in a viewport comprising the first image.

16. The system of claim 1, wherein focusing the second field of view on the area corresponding to the location of the ROI in the second image comprises applying a scaling factor to the area corresponding to the location of the ROI.

17. A method comprising:
receiving, at an image review device, a selection of a region of interest (ROI) in a first image of a plurality of images;

identifying, using an auto-focus tool, a location of the ROI within the first image based on at least one of spacing of image pixel data, thickness of a slice image, and location of the slice image;

converting, via a mapping function of the auto-focus tool, first ROI identification information of the first image to second ROI identification of at least a second image of the plurality of images, wherein the first ROI identification information and the second ROI identification information are a different type, the first ROI identification information includes image view information and the second ROI identification information includes image header information;

identifying, using the auto-focus tool, an area corresponding to the location of the ROI in at least the second image of the plurality of images, wherein the first image and the second image are different imaging modality types and an automated determination mechanism is used to identify the area corresponding to the location of the ROI; and causing the auto-focus tool to automatically:

focus a first field of view on the ROI in the first image; and focus a second field of view on the area corresponding to the location of the ROI in the second image.

18. The method of claim 1, wherein the plurality of images comprises at least a mammography image, an MRI image, and an ultrasound image.

19. A computing device comprising:

a processor; and an image auto-focus tool configured to:

receive a selection of a region of interest (ROI) in a first image of a plurality of images;

identify a location of the ROI within the first image based on at least one of spacing of image pixel data, thickness of a slice image, and location of the slice image;

convert, via a mapping function of the auto-focus tool, first ROI identification information of the first image to second ROI identification of at least a second image of the plurality of images, wherein the first ROI identification information and the second ROI identification information are a different type, the first ROI identification information includes image view information and the second ROI identification information includes image header information;

identify an area corresponding to the location of the ROI in at least the second image of the plurality of images, wherein the first image and the second image are different imaging modality types and an automated determination mechanism is used to identify the area corresponding to the location of the ROI;

focus a first field of view on the ROI in the first image; and focus a second field of view on the area corresponding to the location of the ROI in the second image, wherein focusing the second field of view comprises at least one of scaling the second image or panning the second image.

* * * * *